(12) United States Patent
Han et al.

(10) Patent No.: US 7,956,239 B2
(45) Date of Patent: Jun. 7, 2011

(54) **QTL CONTROLLING *SCLEROTINIA* STEM ROT RESISTANCE IN SOYBEAN**

(75) Inventors: Feng Han, Johnston, IA (US); Maria Katt, Lenexa, KS (US); Wolfgang Schuh, West Des Moines, IA (US); David M. Webb, Zionsville, IN (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 1082 days.

(21) Appl. No.: 11/788,518

(22) Filed: Apr. 20, 2007

(65) Prior Publication Data
US 2008/0227091 A1    Sep. 18, 2008

Related U.S. Application Data

(62) Division of application No. 10/165,617, filed on Jun. 7, 2002, now Pat. No. 7,250,552.

(60) Provisional application No. 60/297,044, filed on Jun. 7, 2001.

(51) Int. Cl.
*A01H 1/04* (2006.01)

(52) U.S. Cl. .................................. 800/267; 800/312

(58) Field of Classification Search .............. 800/266, 800/267, 312
See application file for complete search history.

(56) References Cited

U.S. PATENT DOCUMENTS
6,399,855 B1    6/2002 Beavis

FOREIGN PATENT DOCUMENTS
| CA | 2384838 A1 | 3/2001 |
| CA | 2064077 C | 3/2002 |
| CA | 2119557 C | 2/2004 |
| WO | WO 98/13478 A2 | 4/1998 |
| WO | WO 01/49104 A2 | 7/2001 |

OTHER PUBLICATIONS

Arahana et al. Crop Sci. 41: 180-188, 2001.*
Concibido et al. (2003) "Introgression of a quantitative trait locus for yield from *Glycine soja* into commercial soybean cultivars." *Theoretical and Applied Genetics*, 106: 575-582.
Haussmann et al. (2004) "Plant genetic resources in crop improvement." *Plant Genetic Resources*, 2(1): 3-21.
Shoemaker et al. (2001) "RFLP map of soybean." *DNA-Based Markers in Plants*, Chapter 21; 357-378.
Stuber et al.(1999) "Synergy of Empirical Breeding, Marker-Assisted Selection, and Genomics to Increase Crop Yield Potential." *Crop Science*, 39: 1571-1583.
Young (1996) "QTL Mapping and Quantitative Disease Resistance in Plants." *Annual Review of Phytopathology*, 34: 479-501.
Arahana, Venancio S.; Identification of QTLs for Resistance to *Sclerotinia sclerotiorum* in Soybean, (2001) Crop Sci. 41-180-188.
Alexander et al. (1993) "Increased tolerance to two oomysete pathogens in transgenic tobaco expressing pathogenesis-related protein 1a." *Proc. Natl. Acad. Sci. USA* 90:7327-7331.
Blechert et al. (1995) "The octadecanoic pathway: Signal molecules for the regulation of secondary pathways." *Proc. Natl. Acad. Sci. USA* 92:4099-4105.
Chou and Kutchan (1998) "Enzymatic oxidations in the biosynthesis of complex alkaloids." *The Plant Journal* 15:289-300.
Cline and Coscia (1988) "Stimulation of Sanguinarine Production by Combined Fungal Elicitation and Hormonal Deprivation in Cell Suspension Cultures of *Papaver bracteatum*." *Plant Physiol* 86:0161-0165.
Cregan et al. (1994) "Microsatallite Fingerprinting and Mapping of Soybean." *Methods in Mollecular Cell Biology* 5:49-61.
Dittrich and Kutchan (1991) "Molecular cloning, expression, and induction of berberine bridge enzyme, an enzyme essential to the formation of benzophenanthridine alkaloids in the response of plants to pathogenic attack." *Proc. Natl. Acad. Sci. USA* 88:9969-9973.
Eilert et al. (1985) "Stimulation of Sanguinarine Accomulation of *Papaver somniferum* Cell Cultures by Fungal Elicitors." *Journal Plant Physiology* 119:65-76.
Facchini et al. (1996) "Uncoupled Defense Gene Expression and Antimicrobial Alkaloid Accumulation in Elicited Opium Poppy Cell Cultures." *Plant Physiol*.111:687-697.
Haley and Knott (1992) "A simple regression method for mapping quantitative trait loci line crosses using flanking markers." *Heredity* 69:315-324.
Jansen (1994) "Controlling the Type I and Type II Errors in Mapping Quantitative Trait Loci." *Genetics* 138:871-881.
Keim and Shoemaker (1998) "Construction of a random DNA library that is primarily single copy sequences." *Soybean Genet Newslett.* 15:147-148.
Kim and Diers (2000) "Inheritance of Partial Resistance to *Sclerotinia* Stem Rot in Soybean." *Crop Sci* 40:55-61.
Kim et al. (1999) "Evaluation of Soybean Cultivars for Resistance to *Sclerotinia* Stem Rot in Field Environments." *Crop Sci.* 39:64-68.
Kutchan (1993) "12-Oxo-Phytodienoic Acid Induces Accumulation of Berberine Bridge Enzyme Transcript in a Manner Analogous to Methyl Jasmonate." *J. Plant Physiol.* 142:502-505.
Kutchan and Dittrich (1995) "Characterization and Mechanism of the Berberine Bridge Enzyme, a Covalently Flavinylated Oxidase of Benzophenanthridine Alkaloid Biosynthesis in Plants." *The Journal of Biology Chemistry* 270(14):24475-24481. Lander and Bostein (1989) "Mapping Mendelian Factors Underlying Quantitative Traits Using RFLP Linkage Maps." *Genetics* 121:185-199.
Manly (1993) "RI Manager, a microcomputer program for analysis of data from recombinant inbred strains." *Mammalian Genome* 1:123-126.
Manly and Olson (1999) "Overview of QTL mapping software and introduction to Map Manager QT." *Mammalian Genome* 10:327-334.
Niderman et al. (1995) "Pathogenesis-Related Pr-1 Proteins Are Antifungal," *Plant Physiol* 108:17-27.
Schumacher et al. (1987) "Elicitation of benzophenanthridine alkaloid synthesis in *Eschscholtzia* cell cultures." *Plant Cell Reports* 6:410-413.
Kim et al. (2000) "Isolation and Differential Expression of an Acidic PR-1 cDNA Gene from Soybean Hypocotyls Infected with *Phytophthora sojae* f. sp. *Glycines*," *Plant Patholo. J.*, 16(1): 9-18.
Shoemaker et al. "Public Soybean EST Project." GenBank Accession No. BE803700, *Glycine max* cDNA clone (Jul. 13, 2004).
Qutob et al. (May 2000) "Comparative Analysis of Expressed Sequences in *Phytophthora sojae*," *Plant Physiology*, 123:243-253.

* cited by examiner

*Primary Examiner* — David T Fox
*Assistant Examiner* — Keith O. Robinson
(74) *Attorney, Agent, or Firm* — Potter Anderson & Corroon LLP; Travis W. Bliss

(57) ABSTRACT

Markers associated with *Sclerotinia* stem rot resistance are provided. Methods of identifying resistant, and susceptible plants, using the markers are provided. Methods for identifying and isolating QTL are a feature of the invention, as are QTL associated with *Sclerotinia* stem rot resistance.

9 Claims, 7 Drawing Sheets

QTL CONTROLLING *SCLEROTINIA* STEM ROT RESISTANCE IN SOYBEAN

CROSS-REFERENCE TO RELATED APPLICATIONS

This application is a divisional application under 35 U.S.C. §121 of U.S. patent application Ser. No. 10/165,617, filed on Jun. 7, 2002 (issued as U.S. Pat. No. 7,250,552 on Jul. 31, 2007), which claims the benefit of U.S. Provisional Patent Application Ser. No. 60/297,044, filed Jun. 7, 2001, the disclosures of which are incorporated herein by reference in their entirety for all purposes.

FIELD OF THE INVENTION

The present invention relates generally to plant molecular biology. More specifically, it relates to nucleic acid markers for identification of quantitative trait loci (QTL) associated with *Sclerotinia* stem rot resistance in dicotolydenous plants.

BACKGROUND OF THE INVENTION

*Sclerotinia* stem rot in soybean, also know as white mold, is caused by the fungus pathogen *Sclerotinia sclerotiorum*. The disease was first reported in Hungary in 1924, and has since been reported in many other countries, including the USA. The disease has become increasingly important in the USA since 1990. For example, *Sclerotinia* stem rot caused an estimated yield loss of $6.4 \times 10^5$ metric tons in the USA during 1994 (Wrether et al. (1997) *Plant Dis* 81:107-110). Yield has been shown to be inversely correlated with the percent incidence of *Sclerotinia* stem rot. Yield loss has been estimated at 250 kg/ha for each 10% increment in diseased plants (Grau and Hartman (1999) *Compendium of Soybean Diseases*, 4$^{th}$ ed. APS Press, St. Paul, Minn., USA, pp. 46-48).

*S. sclerotiotum* infects soybean plants in the form of ascospores that land on flowers (Grau (1988) *Am Phytopathol Soc*, St. Paul, Minn., USA pp 56-66). The ascospores germinate under adequate moisture condition and use the flower petals as a nutrient base. Stem lesions originate at leaf axils where flowers are positioned and advance up and down the stem. Symptoms of the *Sclerotinia* stem rot begin to develop at growth stages R2 and R3. Lesions are most frequently on the main stem and completely encircle the stem and disrupt the transport of water, mineral nutrients, and photosynthates to developing pods. Pod development and pod fill above stem lesions are reduced, resulting in yield reduction.

Soybean genotypes show large variations in resistance to *Sclerotinia* stem rot (Kim et al. (1999) *Crop Sci* 39:64-68). So far, no soybean genotypes with complete resistance to *S. sclerotiorum* have been identified. The heritability of partial resistance, measured with a disease severity index (DSI), was estimated to be 0.59 with significant genotype and environment interaction observed (Kim and Diers (2000) *Crop Sci* 40:55-61). Quantitative trait loci ("QTL") analysis identified three QTL explaining 10, 9, and 8% of the variability for DSI across environments and locating on linkage groups C2, K, and M. Two of the QTLs were also significantly associated with disease escape mechanisms such as plant height, and date of flowering.

Breeding for white mold resistance via the traditional approach has been very difficult, due to the multigenic nature of this trait. What is needed in the art is a means to identify genes conferring resistance to white mold, using molecular markers. These markers can then be used to tag the favorable alleles of these genes in segregating dicot populations and then employed to make selection for resistance more effective. The present invention provides this and other advantages.

SUMMARY OF THE INVENTION

The present invention provides methods and markers for identifying Quantitative Trail Loci ("QTL") associated with *Sclerotinia* stem rot resistance in soybeans and other plants. A first aspect of the invention relates to isolated or recombinant nucleic acids corresponding to marker loci useful for the identification and isolation (e.g., by positional cloning) of QTL associated with *Sclerotinia* stem rot resistance in plants, particularly soybean. Such nucleic acid markers include: Satt155, SLS1C.L24, Sat_129, Satt329, Satt556, P1694, PHP8701R, Satt311, PHP10118C, Satt231, P1047, A724_1, Satt523, or SLS2C.F20, and homologous nucleic acids.

In another aspect, the invention relates to methods of identifying a *Sclerotinia* stem rot resistant soybean. In some embodiments, the methods include identifying a *Sclerotinia* stem rot resistant soybean by identifying a QTL associated with resistance by detecting nucleic acids in a soybean plant (or tissue of the soybean plant, e.g., a whole plant, a plant organ, a plant seed or a plant cell) that are genetically linked to a locus proximal to the QTL. The detected nucleic acids typically correspond to marker loci, such as the following simple sequence repeat (SSR) and restriction fragment length polymorphism (RFLP) marker loci: Satt155, SLS1C.L24, Sat_129, Satt329, Satt556, P1694, PHP8701R, Satt311, PHP10118C, Satt231, P1047, A724_1, Satt523, and/or SLS2C.F20. In an embodiment, linked pairs of nucleic acids are detected. For example, in one embodiment, nucleic acids that are homologous to the following pairs of markers: a) Satt155 and SLS1C.L24; b) Sat_129 and Satt329; c) Satt556 and P1694; d) PHP8701R and Satt311; e) PHP10118C and Satt231; f) P1047 and A724_1; org) Satt523 and SLS2C.F20, are detected. In another embodiment, nucleic acids that are at least about 80% identical to one of the above-listed markers are detected.

In some methods, plants identified as described above are crossed with plants lacking the detected nucleic acids. In some cases, *Sclerotinia* stem rot resistance is introgressed into progeny of the cross, i.e., the detected nucleic acid is transmitted to at least a subportion of the progeny derived from the cross.

Following identification of a QTL, nucleic acids corresponding to the QTL can be isolated by positional cloning, for example, by providing a nucleic acid genetically linked to a locus homologous to one of the markers listed above, and then cloning the nucleic acid. In some embodiments, the isolated or recombinant nucleic acid is a QTL localized to a chromosome interval defined by loci homologous to markers a) Satt155 and SLS1C.L24; b) Sat_129 and Satt329; c) Satt556 and P1694; d) PHP8701R and Satt311; e) PHP10118C and Satt231; f) P1047 and A724_1; and g) Satt523 and SLS2C.F20.

Another aspect of the invention relates to compositions comprising isolated or recombinant nucleic acids comprising QTL associated with *Sclerotinia* stem rot resistance in plants, such as soybean. The isolated or recombinant nucleic acids correspond to genomic loci localized within a chromosome interval flanked by loci having at least about 80% sequence identity to a pair of markers selected from among: a) Satt155 and SLS1C.L24; b) Sat_129 and Satt329; c) Satt556 and P1694; d) PHP8701R and Satt311; e) PHP10118C and Satt231; f) P1047 and A724_1; or g) Satt523 and SLS2C.F20. In certain embodiments, the isolated or recombinant nucleic acids correspond to loci localized to a chromosome interval flanked by marker loci having at least about 90%, (or at least about 95%, or at least about 98% or more) identity to one of the above-listed pairs of markers. In some embodiments, marker loci are identical to the above-listed sequences. In some embodiments, sequence identity is determined by the GAP algorithm under default parameters.

In preferred embodiments, the marker pair of (a) is on linkage group A1, (b) is on linkage group A2, (c) is on linkage group B2, (d) is on linkage group D2, (e) is on linkage group E, (f) is on linkage group J, and/or (g) is on linkage group L.

Host cells, and transgenic plants (particularly soybean plants) comprising the isolated or recombinant nucleic acids described above are also a feature of the invention.

Similarly, methods for making transgenic plants, particularly dicots, e.g., transgenic soybeans, are a feature of the invention. Such methods involve introducing an isolated or recombinant nucleic acid corresponding to a QTL associated with *Sclerotinia* stem rot resistance, as described above, into a plant cell, and growing the cell under conditions suitable for growth and, optionally, regeneration of a transgenic plant. In some embodiments, the transgenic plant is crossed with a second plant of the same species, e.g., soybean, sunflower, canola or alfalfa.

In another aspect, the invention relates to methods of identifying candidate QTL associated with *Sclerotinia* stem rot resistance from plants, particularly dicots. Such methods involve providing an isolated or recombinant nucleic acid corresponding to a QTL as described above, and identifying a homolog of the nucleic acid in a plant, such as a dicot. In one embodiment, the isolated or recombinant nucleic acids are provided, and the homolog is identified in silico. In another embodiment the isolated or recombinant nucleic acids are provided, and the homolog is identified by nucleic acid hybridization under selective hybridization conditions. In some embodiments, the homolog is isolated, e.g., cloned.

DETAILED DISCUSSION

Overview

Figure 1:
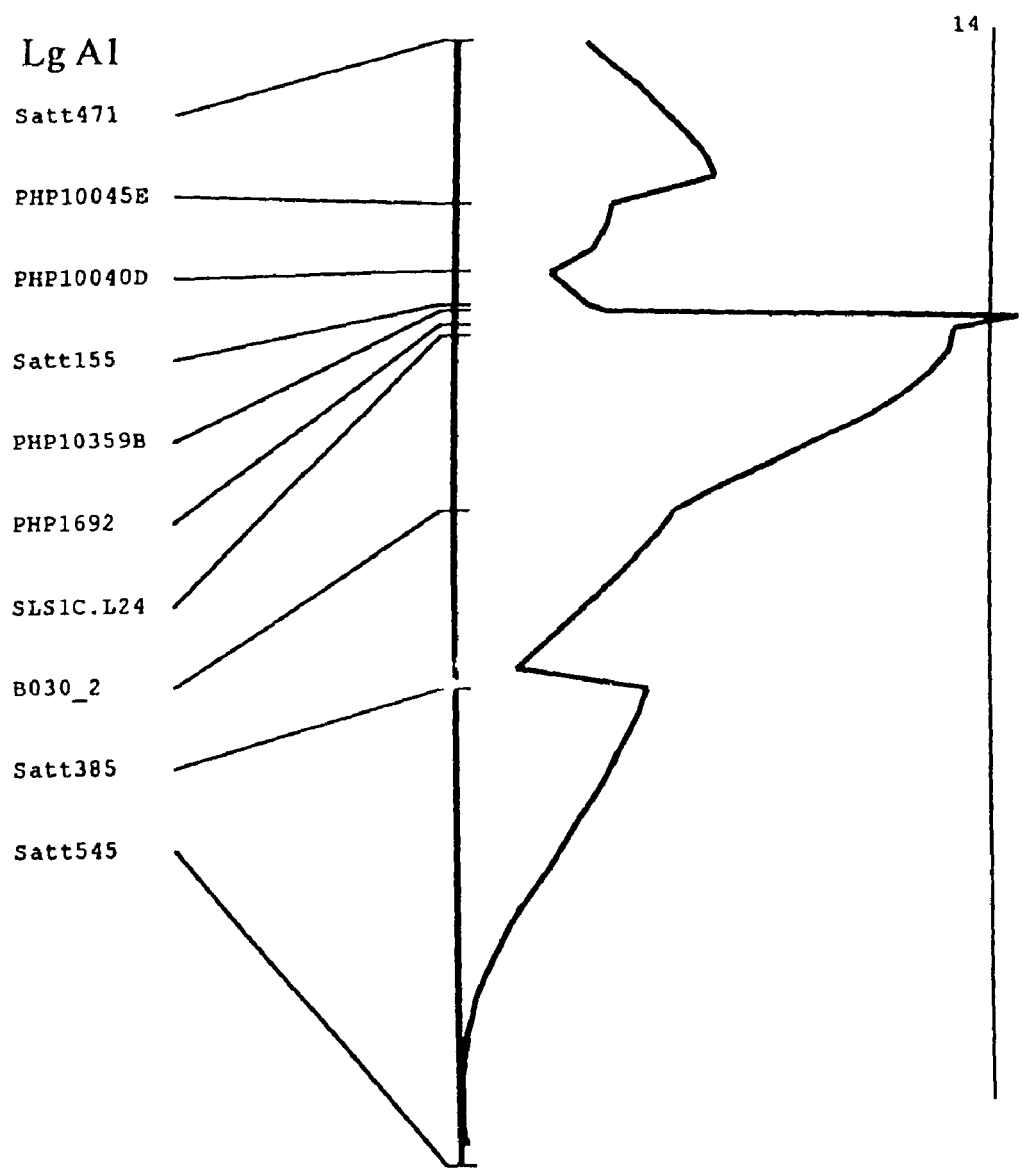
FIG. 1 shows a QTL likelihood map for *Sclerotinia* stem rot resistance on soybean linkage group A1. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval of Satt155-SLS1C.L24 with a distance of 1.3 centiMorgans (cM).

The present invention relates to the identification of genetic markers, e.g., marker loci and nucleic acids corresponding to (or derived from) these marker loci, such as probes and amplification products useful for genotyping plants, correlated with *Sclerotinia* stem rot resistance. The markers of the invention are used to identify plants, particularly plants of the species *Glycine max* (soybean), that are resistant or exhibit improved resistance to *Sclerotinia* stem rot, or white mold. Accordingly, these markers are useful for marker-assisted selection and breeding of *Sclerotinia* stem rot resistant plants, and for identification of susceptible plants. The markers of the invention are also used to identify and define chromosome intervals corresponding to, or including, quantitative trait loci associated with *Sclerotinia* stem rot resistance. Quantitative Trait Loci (QTL) associated with *Sclerotinia* stem rot resistance are isolated by positional cloning, e.g., of genetic intervals defined by a pair of markers described herein, or subsequences of an interval defined by and including such markers. Such isolated QTL nucleic acids can be used for the production of transgenic cells and plants exhibiting improved resistance to *Sclerotinia*. In addition, QTL nucleic acids isolated from one organism, e.g., soybean, can, in turn, serve to isolate homologs of QTLs for *Sclerotinia* stem rot resistance from other susceptible organisms, including a variety of commercially important dicots, such as canola, alfalfa, and sunflower.

Definitions

Units, prefixes, and symbols are denoted in their International System of Units (SI) accepted form. Unless otherwise indicated, nucleic acids are written left to right in 5' to 3' orientation; and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limitations to the various objects and embodiments of the present invention.

The term "quantitative trait locus" or "QTL" refers to a polymorphic genetic locus with at least two alleles that differentially affect the expression of a continuously distributed phenotypic trait.

The term "associated with" or "associated" in the context of this invention refers to, e.g., a nucleic acid and a phenotypic trait, that are in linkage disequilibrium, i.e., the nucleic acid and the trait are found together in progeny plants more often than if the nucleic acid and phenotype segregated separately.

The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci that are in linkage disequilibrium and statistically determined not to assort independently. Genetically linked loci assort dependently from 51% to 99% of the time or any whole number value therebetween, preferably at least 60%, 70%, 80%, 90%, 95% or 99%.

The term "proximal" means genetically linked, typically within about 20 centiMorgans (cM).

The term "marker" or "molecular marker" refers to a genetic locus (a "marker locus") used as a point of reference when identifying genetically linked loci such as a QTL. The term also refers to nucleic acid sequences complementary to the genomic sequences, such as nucleic acids used as probes.

The term "interval" refers to a continuous linear span of chromosomal DNA with termini defined by and including molecular markers.

The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 80% sequence identity, preferably at least 90% sequence identity, and most preferably 95%, 97%, 99%, or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., WO/1993/022443.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction."

The term "host cell" means a cell which contains a heterologous nucleic acid, such as a vector, and supports the replication and/or expression of the nucleic acid. Host cells may be prokaryotic cells such as E. coli, or eukaryotic cells such as yeast, insect, amphibian, or mammalian cells. Preferably, host cells are monocotyledonous or dicotyledonous plant cells. In the context of the invention, one particularly preferred monocotyledonous host cell is a soybean host cell.

The term "transgenic plant" refers to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (i.e., crosses) or by naturally occurring events such as random cross-fertilization, non-recombinant viral infection, non-recombinant bacterial transformation, non-recombinant transposition, or spontaneous mutation.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" in the context of this invention means the fusion of gametes via pollination to produce progeny (i.e., cells, seeds, or plants). The term encompasses both sexual crosses (the pollination of one plant by another) and selfing (self-pollination, i.e., when the pollen and ovule are from the same plant).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

Markers

The present invention provides molecular markers genetically linked to quantitative trait loci ("QTL") associated with resistance to *Sclerotinia* stem rot, also known as white mold. Such molecular markers are useful for identifying and producing dicotyledonous plants, in particular, such commercially important dicot crops as sunflower, canola, alfalfa, and soybean, resistant, or with improved resistance, to *Sclerotinia* stem rot.

Genetic mapping of over 300 molecular markers has developed a genetic linkage map covering approximately 2400 cM (centiMorgans) corresponding to the 20 soybean chromosomes. Of 331 markers mapped, 53 are restriction fragment length polymorphisms (RFLP), 159 are amplified fragment length polymorphisms (AFLP), 21 are proprietary (Dupont) simple sequence repeat (SSR) polymorphisms, and 100 are public SSR polymorphisms. Additional details regarding the nature and use of molecular markers are provided below in the section entitled "MARKER ASSISTED SELECTION AND BREEDING."

Exemplary marker loci associated with resistance to *Sclerotinia* stem rot are localized to seven linkage groups in soybean: A1, A2, B2, D2, E, J, and L. These exemplary marker loci delineate chromosomal intervals including Quantitative Trait Loci (QTL) associated with phenotypic measures of resistance to *Sclerotinia* stem rot. For example: Satt155 and SLS1C.L24 localize to linkage group A1; Sat_129 and Satt329 localize to linkage group A2; Satt556 and P1694 localize to linkage group B2; PHP8701R and Satt311 localize to linkage group D2; PHP10118C and Satt231 localize to linkage group E; P1047 and A724_1 localize to linkage group J; and Satt523 and SLS2C.F20 localize to linkage group L.

Simple sequence repeat (SSR) markers P1694, Sat-129, Satt155, Satt231, P1047, Satt311, Satt329, PHP10118C, Satt523, and Satt556 are discussed in Cregan et al. (1994) *Meth. Mol. Cell. Biol.* 5:49-61, are available from the Soy-Base internet database established by the United States Department of Agriculture (SoyBase, G304 Agronomy Hall Iowa State University, Ames, Iowa). Primers suitable for amplification of polymorphic products corresponding to these marker loci are provided in Table 1. Additional primers and probes corresponding to these markers can be designed based on the sequence information provided hereinbelow (SEQ ID NO:24-33). In addition, substitute primers and probes for markers P1694, PHP10118C and P1047 can be selected based on the sequences of the linked publicly available markers Satt063, Sat_124, and Satt596, respectively.

Marker A724_1 is detectable as an RFLP using a publicly available probe (SoyBase, G304 Agronomy Hall Iowa State University, Ames, Iowa; internet address: http://129.186.26.94).

SLS1C.L24 (SEQ ID NO:1) and SLS2C.F20 (SEQ ID NO:2) are novel expressed sequence tag (EST) markers used as probes for detecting restriction fragment length polymorphisms, e.g., by Southern analysis.

PHP8701R (SEQ ID NO:3) is a novel marker locus detected as an amplified fragment length polymorphism.

TABLE 1

Primers for amplification of Marker Loci

| Marker | Forward Primer | Reverse Primer |
|---|---|---|
| P1694 | TGTCAATAAATGGCTAATCG (SEQ ID NO: 4) | TGGTAGTTTTCACACGTTA TG (SEQ ID NO: 5) |
| Sat_129 | TTCAGTACAAGTCGGGTGAA TAATAATA (SEQ ID NO: 6) | TCACATGTTCGGGACTTAA GGTAT (SEQ ID NO: 7) |
| Satt155 | AGATCCAACACCTGGCCTA AT (SEQ ID NO: 8) | GCTGCACAATTCATTCCAT TT (SEQ ID NO: 9) |
| Satt231 | GCGTGTGCAAAATGTTCATC ATCT (SEQ ID NO: 10) | GGCACGAATCAACATCAAA ACTTC (SEQ ID NO: 11) |
| P1047 | TCGCTTTTAATGACCTCGAC (SEQ ID NO: 12) | CGGAGGATTTGTCATAGAT TC (SEQ ID NO: 13) |
| Satt311 | GGGGGAACCACAAAAATCTT AATC (SEQ ID NO: 14) | GTTGAAGCTCAGGCTGTGA TGAAT (SEQ ID NO: 15) |
| Satt329 | GCGGGACGCAAAATTGGATT TAGT (SEQ ID NO: 16) | GCGCCGAATAAAACGTGAG AACTG (SEQ ID NO: 17) |
| PHP10118C | GACTGCGTACCAATTCACA (SEQ ID NO: 18) | GATGAGTCCTGAGTAACAC (SEQ ID NO: 19) |
| Satt523 | GCGATTTCTTCCTTGAAGAA TTTTCTG (SEQ ID NO: 20) | GCGCTTTTTCGGCTGTTAT TTTTAACT (SEQ ID NO: 21) |
| Satt556 | GCGATAAAACCCGATAAAT AA (SEQ ID NO: 22) | GCGTTGTGCACCTTGTTTT CT (SEQ ID NO: 23) |

It will be noted that, regardless of their molecular nature, e.g., whether the marker is an SSR, AFLP, RFLP, etc., markers are typically strain specific. That is, a particular polymorphic marker, such as the exemplary markers of the invention described above, is defined relative to the parental lines of interest. For each marker locus, resistance-associated, and conversely, susceptibility-associated alleles are identified for each pair of parental lines. Following correlation of specific alleles with susceptibility and resistance in parents of a cross, the marker can be utilized to identify progeny with genotypes that correspond to the desired resistance phenotype. In some circumstances, i.e., in some crosses of parental lines, the exemplary markers described herein will not be optimally informative. In such cases, additional informative markers, e.g., certain linked markers and/or homologous markers are evaluated and substituted for genotyping, e.g., for marker-assisted selection, etc. In the case where a marker corresponds to a QTL, following identification of resistance- and susceptibility-associated alleles, it is possible to directly screen a population of samples, e.g., samples obtained from a seed bank, without first correlating the parental phenotype with an allele.

Linked Markers

Figure 2:
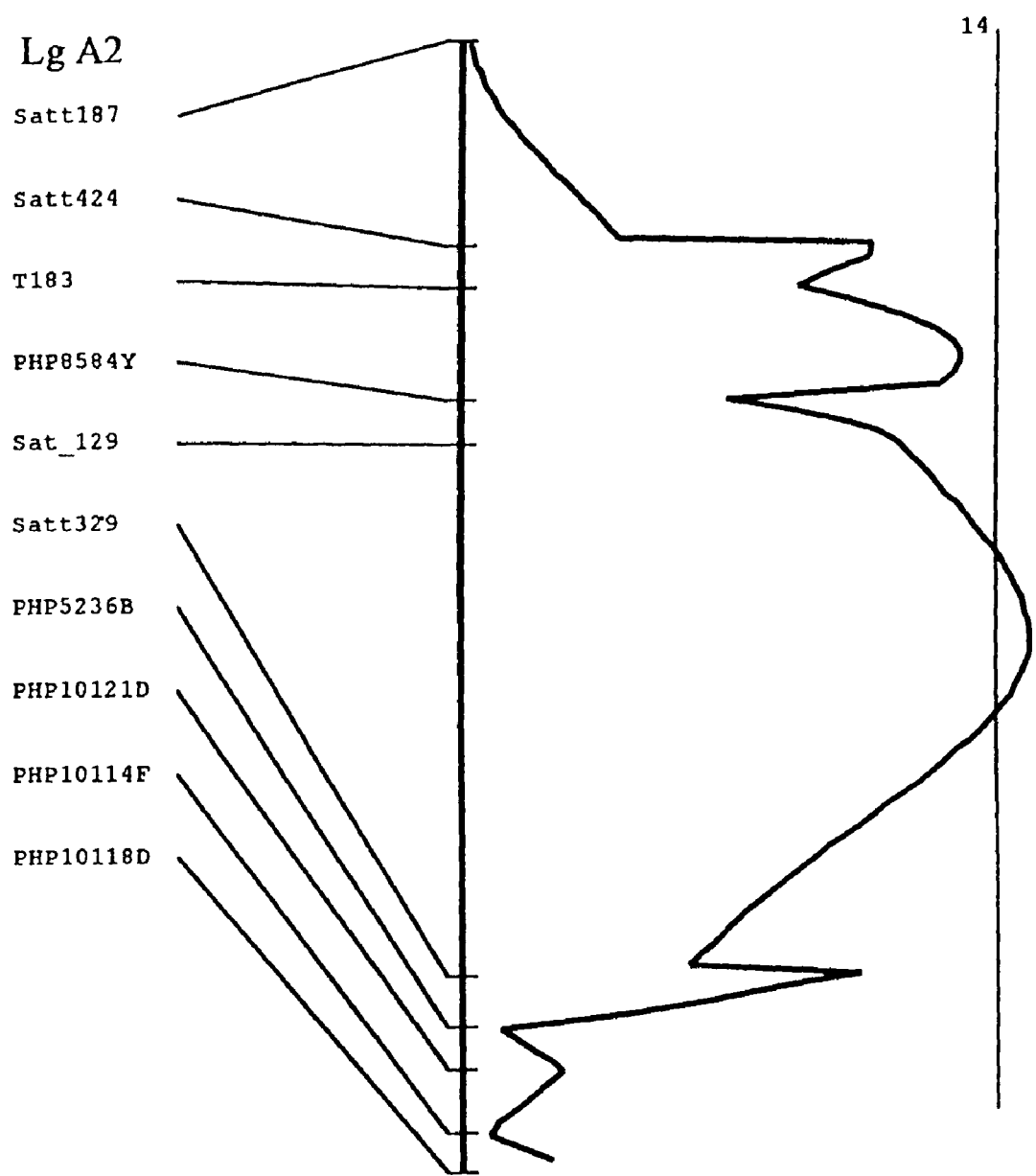
FIG. 2 shows a QTL likelihood map for *Sclerotinia* stem rot resistance on soybean linkage group A2. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval Sat_129-Satt329 with a distance of 31.7 cM.
Figure 3:
FIG. 3 shows a QTL likelihood map for *Sclerotinia* stem rot resistance on soybean linkage group B2. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval Satt556-P1694 with a distance of 12.7 cM.
Figure 4:
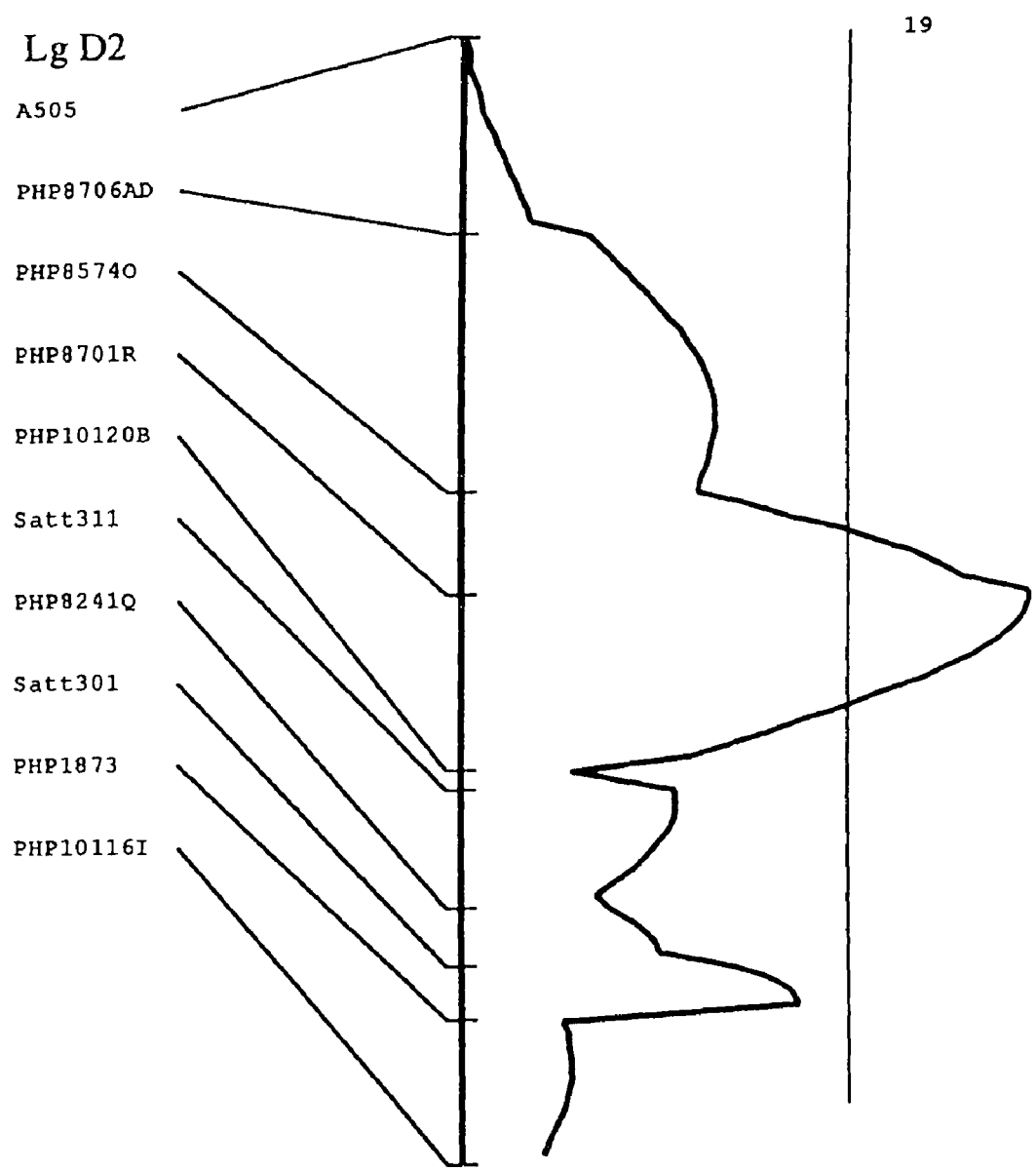
FIG. 4 shows a QTL likelihood map for *Sclerotinia* stem rot resistance on soybean linkage group D2. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval PHP8701R-Satt311 with a distance of 14.5 cM.
Figure 5:
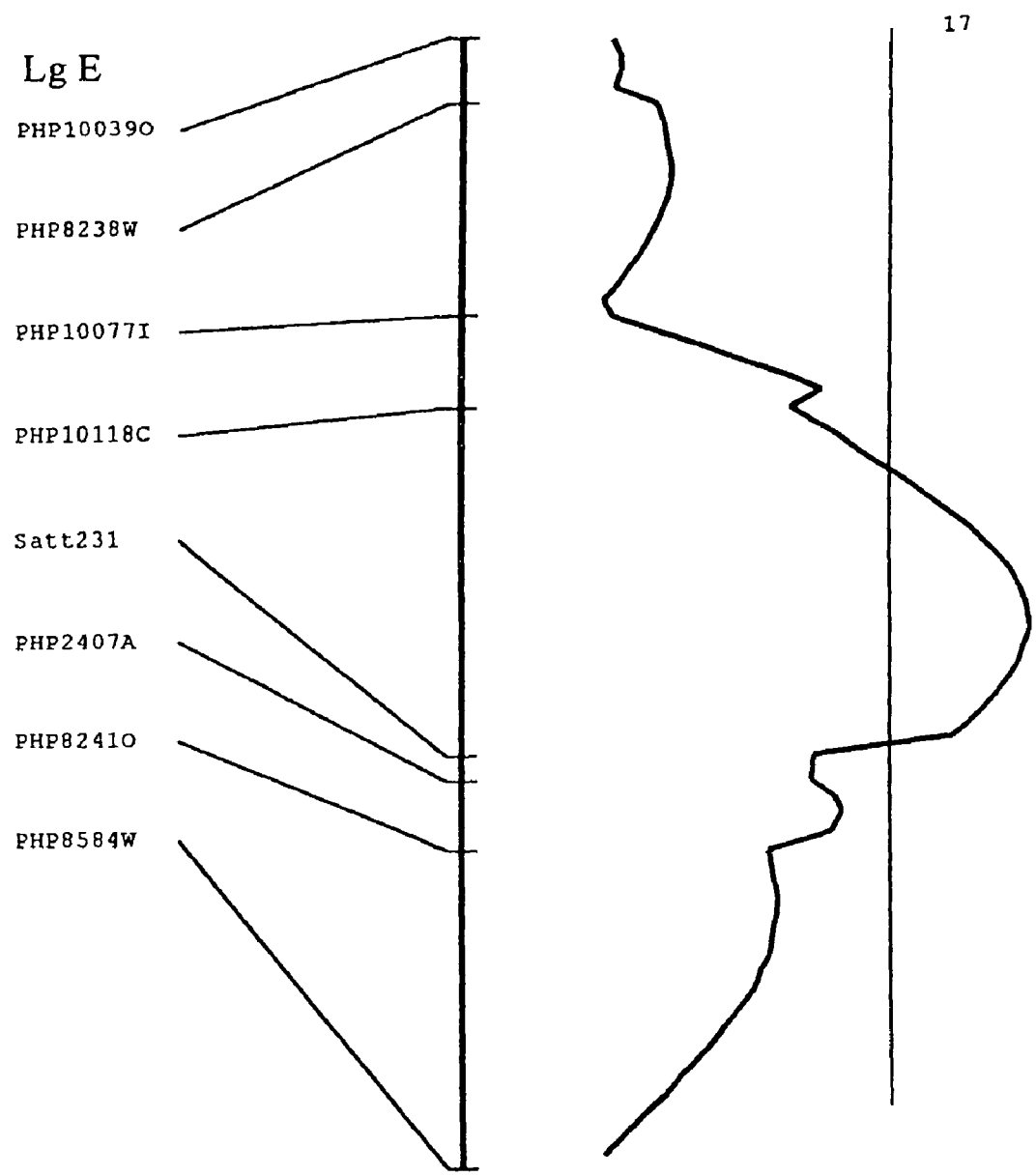
FIG. 5 shows a QTL likelihood map for *Sclerotinia* stem rot resistance on soybean linkage group E. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval PHP10118C-Satt231 with a distance of 18.8 cM.
Figure 6:
FIG. 6 shows a QTL likelihood map for *Sclerotinia* stem rot resistance on soybean linkage group J. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval P1047-A724_1 with a distance of 22.5 cM.
Figure 7:
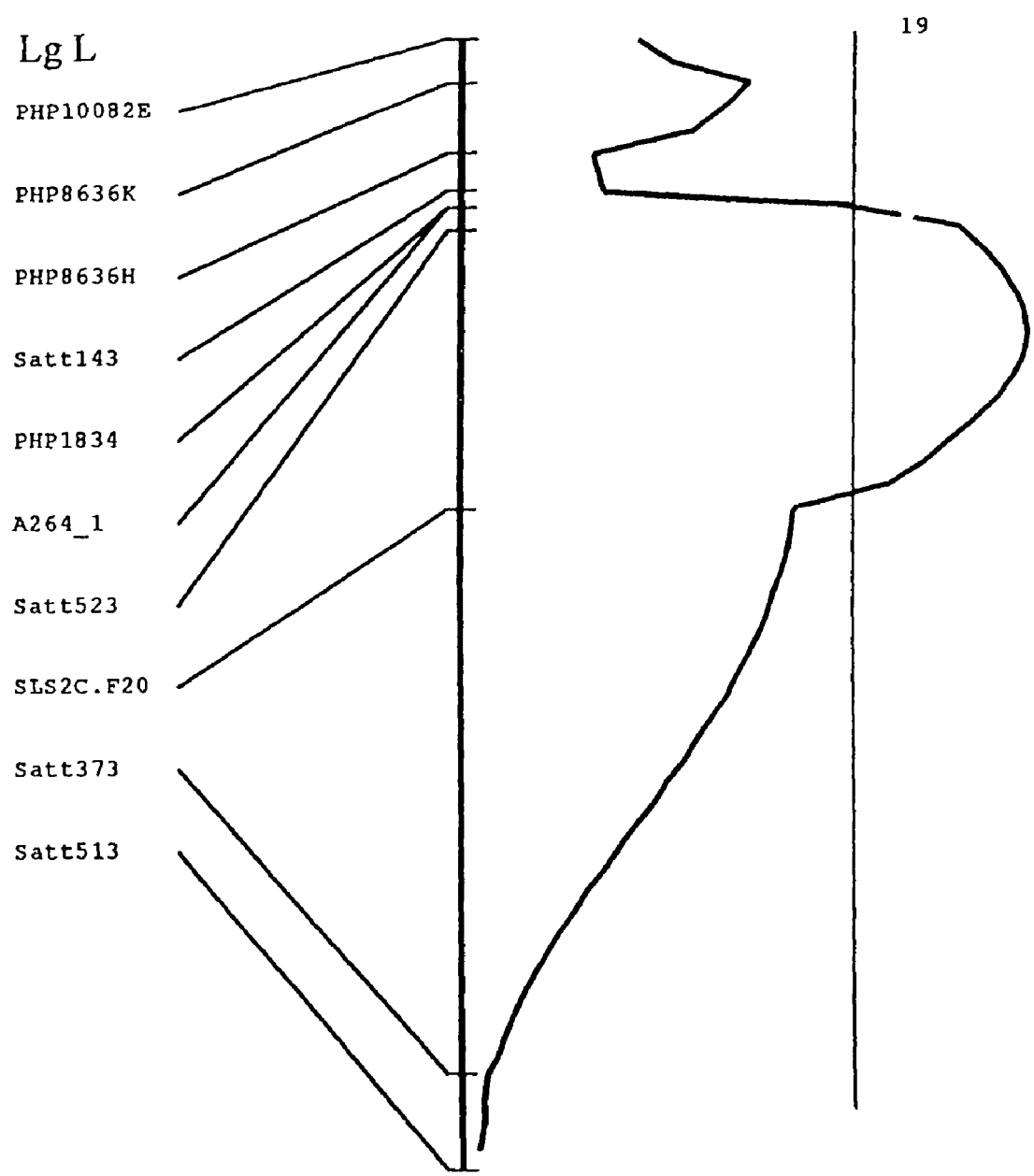
FIG. 7 shows a QTL likelihood map for *Sclerotinia* stem rot resistance on soybean linkage group L. Molecular markers are placed on the left side bar, and a Likelihood Ratio Statistic (LRS) is placed on the right side bar. The number on the upper corner indicates the relative position of the LRS value generated by the MapManager program. The LRS peak of this QTL is in the interval Satt523-SLS2C.F20 with a distance of 11.7 cM.

FIGS. 1-7 provide additional linked markers that can be used in addition to, or in place of: Satt155, SLS1C.L24, Sat_129, Satt329, Satt556, P1694, PHP8701R, Satt311, PHP10118C, Satt231, P1047, A724_1, Satt523, and SLS2C.F20 for the purposes, e.g., of mapping and isolating QTL associated with *Sclerotinia* stem rot. Those of skill in the art will recognize that additional molecular markers can be identified within the intervals defined by the above-described pairs of markers. Such markers are also genetically linked to the QTLs identified herein as associated with *Sclerotinia* rot resistance, and are within the scope of the present invention. Markers can be identified by any of a variety of genetic or physical mapping techniques. Methods of determining whether markers are genetically linked to a QTL (or to a specified marker) associated with resistance to *Sclerotinia* stem rot are known to those of skill in the art and include, e.g., interval mapping (Lander and Botstein (1989) Genetics 121: 185), regression mapping (Haley and Knott (1992) Heredity 69:315) or MQM mapping (Jansen (1994) Genetics 138: 871). In addition, such physical mapping techniques as chromosome walking, contig mapping and assembly, and the like, can be employed to identify and isolate additional sequences useful as markers in the context of the present invention.

Homologous Markers

In addition, Satt155, SLS1C.L24, Sat_129, Satt329, Satt556, P1694, PHP8701R, Satt311, PHP10118C, Satt231, P1047, A724_1, Satt523, and SLS2C.F20 are useful for the identification of homologous marker sequences with utility in identifying QTL associated with *Sclerotinia* stem rot resistance in different lines, varieties, or species of dicots. Such homologous markers are also a feature of the invention.

Homologous markers can be identified by selective hybridization to a reference sequence. The reference sequence is typically a unique sequence, such as unique oligonucleotide primer sequences, ESTs, amplified fragments (e.g., corresponding to AFLP markers) and the like, derived from the marker loci Satt155, SLS1C.L24, Sat_129, Satt329, Satt556, P1694, PHP8701R, Satt311, PHP10118C, Satt231, P1047, A724_1, Satt523, and SLS2C.F20, or its complement.

Two single-stranded nucleic acids "hybridize" when they form a double-stranded duplex. The double stranded region can include the full-length of one or both of the single-stranded nucleic acids, or all of one single stranded nucleic acid and a subsequence of the other single-stranded nucleic acid, or the double stranded region can include a subsequence of each nucleic acid. Selective hybridization conditions distinguish between nucleic acids that are related, e.g., share significant sequence identity with the reference sequence (or its complement) and those that associate with the reference sequence in a non-specific manner. Generally, selective hybridization conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Selective hybridization conditions may also be achieved with the addition of destabilizing agents such as formamide. Selectivity can be achieved by varying the stringency of the hybridization and/or wash conditions. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically a function of post-hybridization washes, with the critical factors being ionic strength and temperature of the final wash solution. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

The $T_m$ is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays" Elsevier, N.Y. General Texts which discuss considerations relevant to nucleic acid hybridization, the selection of probes, and buffer and incubation conditions, and the like, as well as numerous other topics of interest in the context of the present invention (e.g., cloning of nucleic acids which correspond to markers and QTL, sequencing of cloned markers/QTL, the use of promoters, vectors, etc.) can be found in Berger and Kimmel (1987) *Guide to Molecular Cloning Techniques, Methods in Enzymology* vol. 152, Academic Press, Inc., San Diego ("Berger"); Sambrook et al., (2001) *Molecular Cloning—A Laboratory Manual,* 3rd ed. Vols. 1-3, Cold Spring Harbor Laboratory, Cold Spring Harbor ("Sambrook"); and Ausubel et al., (eds) (supplemented through 2001) *Current Protocols in Molecular Biology*, John Wiley and Sons, Inc., ("Ausubel").

In addition to hybridization methods described above, homologs of the markers of the invention can be identified in silico using any of a variety of sequence alignment and comparison protocols. For the purposes of the ensuing discussion, the following terms are used to describe the sequence relationships between a marker nucleotide sequence and a reference polynucleotide sequence:

A "reference sequence" is a defined sequence used as a basis for sequence comparison with a test sequence, e.g., a candidate marker homolog, of the present invention. A reference sequence may be a subsequence or the entirety of a specified sequence; for example, a segment of a full-length cDNA or gene sequence, or the complete cDNA or gene sequence.

As used herein, a "comparison window" is a contiguous and specified segment, (e.g., a subsequence) of a polynucleotide/polypeptide sequence to be compared to a reference sequence. The segment of the polynucleotide/polypeptide sequence in the comparison window can include one or more additions or deletions (i.e., gaps) with respect to the reference sequence, which (by definition) does not comprise addition(s) or deletion(s), for optimal alignment of the two sequences. An optimal alignment of two sequences yields the fewest number of unlike nucleotide/amino acid residues in a comparison window. Generally, the comparison window is at least 20 contiguous nucleotide/amino acid residues in length, and optionally can be 30, 40, 50, 100, or longer. Those of skill in the art understand that to avoid a falsely high similarity between two sequences, due to inclusion of gaps in the polynucleotide/polypeptide sequence, a gap penalty is typically assessed and is subtracted from the number of matches.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue, determining the number of matched positions, dividing the number of matched positions by the total number of positions in the comparison window, and multiplying the result by 100 to yield the percentage of sequence identity.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ by conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) *Computer Applic. Biol. Sci.* 4:11-17, e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci. USA* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp (1988) *Gene* 73:237-244; Higgins and Sharp (1989) *CABIOS* 5:151-153; Corpet et al. (1988) *Nucleic Acids Research* 16:10881-90; Huang et al. (1992) *Computer Applications in the Biosciences* 8: 155-65, and Pearson et al. (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, e.g., *Current Protocols in Molecular Biology*, Chapter 19, Ausubel et al., Eds., (1995) Greene Publishing and Wiley-Interscience, New York; Altschul et al. (1990) *J. Mol. Biol.* 215:403-410; and, Altschul et al. (1997) *Nucleic Acids Res.* 25:3389-3402.

Software for performing BLAST analyses is publicly available, e.g., through the National Center for Biotechnology Information (available on the internet). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, e.g., Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-163) and XNU (Claverie and States (1993) *Comput. Chem.* 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, e.g., Henikoff & Henikoff (1989) *Proc. Natl. Acad. Sci. USA* 89:10915).

Multiple alignment of the sequences can be performed using the CLUSTAL method of alignment (Higgins and Sharp (1989) CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The percentage sequence identity of a homologous marker to its reference marker (e.g., any one Satt155, SLS1C.L24, Sat_129, Satt329, Satt556, P1694, PHP8701R, Satt311, PHP10118C, Satt231, P1047, A724_1, Satt523, and SLS2C.F20) is typically at least 80% and, rounded upwards to the nearest integer, can be expressed as an integer selected from the group of integers between 80 and 99. Thus, for example, the percentage sequence identity to a reference sequence can be at least 80%, 85%, 90%, 95%, 97%, or 99%. Sequence identity can be calculated using, for example, the BLAST, CLUSTALW, or GAP algorithms under default conditions.

Detection of Marker Loci

Markers corresponding to genetic polymorphisms between members of a population can be detected by numerous methods, well-established in the art (e.g., restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP)).

The majority of genetic markers rely on one or more property of nucleic acids for their detection. For example, some techniques for detecting genetic markers utilize hybridization of a probe nucleic acid to nucleic acids corresponding to the genetic marker. Hybridization formats including but not limited to, solution phase, solid phase, mixed phase, or in situ hybridization assays. Markers which are restriction fragment length polymorphisms (RFLP), are detected by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling markers is readily achieved such as by the use of labeled PCR primers to marker loci.

The hybridized probe is then detected using, most typically by autoradiography or other similar detection technique (e.g., fluorography, liquid scintillation counter, etc.). Examples of specific hybridization protocols are widely available in the art, see, e.g., Berger, Sambrook, Ausubel, all supra.

Amplified variable sequences refer to amplified sequenes of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis et al. (1987) U.S. Pat. No. 4,683,202; *PCR Protocols, A Guide to Methods and Applications* (Innis et al., eds.) Academic Press Inc., San Diego Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as primers, e.g., in amplification reactions and for use as nucleic acid sequence probes are typically synthesized chemically according to the solid phase phosphoramidite triester method described by Beaucage and Caruthers (1981) *Tetrahedron Lett.* 22:1859, or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) *Nucl Acids Res* 23:4407. The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol Gen Genet.* 249:65; and Meksem et al. (1995) *Mol Gen Genet.* 249:74.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are not excluded.

In yet another basis for providing a genetic linkage map, Simple sequence repeats (SSR), take advantage of high levels of di-, tri-, or tetra-nucleotide tandem repeats within a genome. Dinucleotide repeats have been reported to occur in the human genome as many as 50,000 times with n varying from 10 to 60 or more (Jacob et al. (1991) *Cell* 67:213. Dinucleotide repeats have also been found in higher plants (Condit and Hubbell (1991) *Genome* 34:66).

Briefly, SSR data is generated by hybridizing primers to conserved regions of the plant genome which flank the SSR sequence. PCR is then used to amplify the dinucleotide repeats between the primers. The amplified sequences are then electorphoresed to determine the size and therefore the number of di-, tri-, and tetra-nucleotide repeats.

Alternatively, isozyme markers are employed as genetic markers. Isozymes are multiple forms of enzymes which differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

In alternative embodiments, in silico methods can be used to detect the marker loci. For example, the sequence of a nucleic acid comprising the marker can be stored in a computer. The desired marker locus sequence or its homolog can be identified using an appropriate nucleic acid search algorithm as provided by, for example, in such readily available programs as BLAST.

QTL Mapping

Multiple experimental paradigms have been developed to identify and analyze QTL. In general, these paradigms involve crossing one or more parental pairs, which can be, for example, a single pair derived from two inbred strains, or multiple related or unrelated parents of different inbred strains or lines, which each exhibit different characteristics relative to the phenotypic trait of interest. The parents, and a population of progeny are genotyped, typically for multiple marker loci, and evaluated for the trait of interest. In the context of the present invention, the parental and progeny plants are genotyped for any one or more of the molecular markers: Satt155, SLS1C.L24, Sat__129, Satt329, Satt556, P1694, PHP8701R, Satt311, PHP10118C, Satt231, P1047, A724__1, Satt523, and SLS2C.F20, or homologues, or alternative markers linked to any one or more of Satt155, SLS1C.L24, Sat__129, Satt329, Satt556, P1694, PHP8701R, Satt31, PHP10118C, Satt231, P1047, A724__1, Satt523, and SLS2C.F20, and evaluated for resistance, or relative resistance to *Sclerotinia* stem rot. QTL associated with *Sclerotinia* stem rot resistance are identified based on the significant statistical correlations between the marker genotype(s) and the resistance phenotype of the evaluated progeny plants. Numerous methods for determining whether markers are genetically linked to a QTL (or to another marker) associated with resistance to *Sclerotinia* stem rot are known to those of skill in the art and include, e.g., interval mapping (Lander and Botstein (1989) *Genetics* 121:185), regression mapping (Haley and Knott (1992) *Heredity* 69:315) or MQM mapping (Jansen (1994) *Genetics* 138:871). In addition, the following applications provide additional details regarding alternative statistical methods applicable to complex breeding populations which can be used to identify and localize QTLs associated with *Sclerotinia* stem rot resistance: U.S. Pat. No. 6,399,855, issued Jun. 4, 2002, by Beavis et al. "QTL MAPPING IN PLANT BREEDING POPULATIONS" and WO 2001/049104, published Jul. 12, 2001, by Jansen et al. "MQM MAPPING USING HAPLOTYPED PUTATIVE QTLS ALLELES: A SIMPLE APPROACH FOR MAPPING QTLS IN PLANT BREEDING POPULATIONS."

Marker Assisted Selection and Breeding of Plants

A primary motivation for development of molecular markers in crop species is the potential for increased efficiency in plant breeding through marker assisted selection (MAS). Genetic marker alleles, or alternatively, identified QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly dicots, e.g., soybean, that are resistant, or exhibit improved resistance, to *Sclerotinia* stem rot by identifying plants having a specified allele, e.g., at markers Satt155, SLS1C.L24, Sat__129, Satt329, Satt556, P1694, PHP8701R, Satt311, PHP10118C, Satt231, P1047, A724__1, Satt523, and SLS2C.F20, or homologous or linked markers. Similarly, by identifying plants lacking the desired allele, susceptible plants can be identified, and, e.g., eliminated from subsequent crosses. It will be appreciated that for the purposes of MAS, the term marker can encompass both marker and QTL loci as both can be used to identify plants with that are resistant or have improved resistance to *Sclerotinia* stem rot.

After a desired phenotype, e.g., *Sclerotinia* stem rot resistance, and a polymorphic chromosomal locus, e.g., a marker locus or QTL, are determined to segregate together, it is possible to use those polymorphic loci to select for alleles corresponding to the desired phenotype-a process called marker-assisted selection (MAS). In brief, a nucleic acid corresponding to the marker nucleic acid is detected in a biological sample from a plant to be selected. This detection can take the from of hybridization of a probe nucleic acid to a marker, e.g., using allele-specific hybridization, Southern analysis, northern analysis, in situ hybridization, hybridization of primers followed by PCR amplification of a region of the marker or the like. A variety of procedures for detecting markers are described herein, e.g., in the section entitled "*DETECTION OF MARKER LOCI.*" After the presence (or absence) of a particular marker in the biological sample is verified, the plant is selected, i.e., used to make progeny plants by selective breeding.

Soybean breeders need to combine disease resistance loci with genes for high yield and other desirable traits to develop improved soybean varieties. Disease screening for large numbers of samples can be expensive, time consuming, and unreliable. Use of the polymorphic loci described herein, and genetically-linked nucleic acids, as genetic markers for disease resistance loci is an effective method for selecting resistant varieties in breeding programs. For example, one advantage or marker-assisted selection over field evaluations for disease resistance is that MAS can be done at any time of year regardless of the growing season. Moreover, environmental effects are irrelevant to marker-assisted selection.

When a population is segregating for multiple loci affecting one or multiple traits, e.g., multiple loci involved in resistance to single disease, or multiple loci each involved in resistance to different diseases, the efficiency of MAS compared to phenotypic screening becomes even greater because all the loci can be processed in the lab together from a single sample of DNA. In the present instance, this means that multiple markers selected from among Satt155, SLS1C.L24, Sat__129, Satt329, Satt556, P1694, PHP8701R, Satt311, PHP10118C, Satt231, P1047, A724__1, Satt523, and SLS2C.F20, or markers homologous or linked thereto can be assayed simultaneously or sequentially in a single sample or population of samples. Thus, any one or more of these markers, e.g., two or more, up to and including all of the established markers, can be assayed simultaneously. In some instances, it is desirable to evaluate a marker corresponding to each of the linkage groups associated with *Sclerotinia* stem rot.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that is done, the greater the genetic contribution of the recurrent parent to the resulting variety. This is often necessary, because resistant plants may be otherwise undesirable, i.e., due to low yield, low fecundity, or the like. In contrast, strains which are the result of intensive breeding programs may have excellent yield, fecundity or the like, merely being deficient in one desired trait such as resistance to a particular pathogen (e.g., *Sclerotinia* stem rot resistance).

The presence and/or absence of a particular genetic marker allele, e.g., Satt155, SLS1C.L24, Sat__129, Satt329, Satt556, P1694, PHP8701R, Satt311, PHP10118C, Satt231, P1047, A724__1, Satt523, and SLS2C.F20, or a homolog thereof, in the genome of a plant exhibiting a preferred phenotypic trait is made by any method listed above, e.g., RFLP, AFLP, SSR, etc. If the nucleic acids from the plant are positive for a desired genetic marker, the plant can be selfed to create a true breeding line with the same genotype, or it can be crossed with a plant with the same marker or with other desired characteristics to create a sexually crossed hybrid generation.

Positional Cloning

The molecular markers of the present invention, e.g., Satt155, SLS1C.L24, Sat__129, Satt329, Satt556, P1694, PHP8701R, Satt311, PHP10118C, Satt231, P1047, A724__1, Satt523, and SLS2C.F20, and nucleic acids homologous thereto, can be used, as indicated previously, to identify additional linked marker loci, which can be cloned by well established procedures, e.g., as described in detail in Ausubel, Berger and Sambrook, supra. Similarly, the markers: Satt155, SLS1C.L24, Sat__129, Satt329, Satt556, P1694, PHP8701R, Satt311, PHP10118C, Satt231, P1047, A724__1, Satt523, and SLS2C.F20, as well as any additionally identified linked molecular markers can be used to physically isolate, e.g., by cloning, nucleic acids associated with QTLs contributing to *Sclerotinia* stem rot resistance. Such nucleic acids, i.e., linked to QTL, have a variety of uses, including as genetic markers for identification of additional QTLs in subsequent applications of marker assisted selection (MAS).

These nucleic acids are first identified by their genetic linkage to markers of the present invention. Isolation of the nucleic acid of interest is achieved by any number of methods as discussed in detail in such references as Ausubel, Berger and Sambrook, supra, and Clark, Ed. (1997) *Plant Molecular Biology: A Laboratory Manual* Springer-Verlag, Berlin.

For example, "Positional gene cloning" uses the proximity of a genetic marker to physically define an isolated chromosomal fragment that is linked to a QTL. The isolated chromosomal fragment can be produced by such well known methods as digesting chromosomal DNA with one or more restriction enzymes, or by amplifying a chromosomal region in a polymerase chain reaction (PCR), or alternative amplification reaction. The digested or amplified fragment is typically ligated into a vector suitable for replication, e.g., a plasmid, a cosmid, a phage, an artificial chromosome, or the like, and, optionally expression, of the inserted fragment. Markers which are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones which together comprise a contiguous sequence of DNA, a "contig." Protocols sufficient to guide one of skill through the isolation of clones associated with linked markers are found in, e.g. Berger, Sambrook and Ausubel, all supra.

Isolated Chromosome Intervals

The present invention provides isolated nucleic acids comprising a QTL associated with *Sclerotinia* stem rot resistance. The QTL is localized within an interval defined by two markers of the present invention wherein each marker flanks and is genetically linked to the QTL. Such intervals can be utilized to identify homologous nucleic acids and/or can be used in the production of transgenic plants having the resistance to *Sclerotinia* stem rot conferred by the introduced QTL. A chromosome interval comprising a QTL is isolated, e.g., cloned via positional cloning methods outlined above. A chromosome interval can contain one or more ORFs associated with resistance, and can be cloned on one or more individual vectors, e.g., depending on the size of the chromosome interval.

It will be appreciated that numerous vectors are available in the art for the isolation and replication of the nucleic acids of the invention. For example, plasmids, cosmids and phage vectors are well known in the art, and are sufficient for many applications (e.g., in applications involving insertion of nucleic acids ranging from less than 1 to about 20 kilobases (kb). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centiMorgans (cM), linked to QTLs as identified herein. In such cases, a number of vectors capable of accommodating large nucleic acids are available in the art, these include, yeast artificial chromosomes (YACs), bacterial artificial chromosomes (BACs), plant artificial chromosomes (PACs) and the like. For a general introduction to YACs, BACs, PACs and MACs as artificial chromosomes, see, e.g., Monaco and Larin (1994) *Trends Biotechnol* 12:280. In addition, methods for the in vitro amplification of large nucleic acids linked to genetic markers are widely available (e.g., Cheng et al. (1994) *Nature* 369: 684, and references therein). Cloning systems can be created or obtained from commercially; see, for example, Stratagene Cloning Systems, Catalogs 2000 (La Jolla, Calif.).

Generation of Transgenic Plants and Cells

The present invention also relates to host cells and organisms which are transformed with nucleic acids corresponding to QTL and other genes identified according to the invention. For example, such nucleic acids include chromosome intervals, ORFs, and/or cDNAs or corresponding to a sequence or subsequence included within the identified chromosome interval or ORF. Additionally, the invention provides for the production of polypeptides corresponding to QTL by recombinant techniques. Host cells are genetically engineered (i.e., transduced, transfected or transformed) with the vectors of this invention (i.e., vectors which comprise QTLs or other nucleic acids identified according to the methods of the invention and as described above) which are, for example, a cloning vector or an expression vector. Such vectors include, in addition to those described above, e.g., an *agrobacterium*, a virus (such as a plant virus), a naked polynucleotide, or a conjugated polynucleotide. The vectors are introduced into plant tissues, cultured plant cells or plant protoplasts by a variety of standard methods including electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407, 956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233; 496; Fraley et al. (1983) *Proc. Natl. Acad. Sci. USA* 80; 4803). The method of introducing a nucleic acid of the present invention into a host cell is not critical to the instant invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. (1983) "Protoplast Isolation and Culture," *Handbook of Plant Cell Cultures* 1, 124-176 (Macmillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton,).

The present invention also relates to the production of transgenic organisms, which may be bacteria, yeast, fungi, or plants, transduced with the nucleic acids, e.g., cloned QTL of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328:731; Schneider et al. (1995) *Protein Expr. Purif.* 6435: 10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA, Second Edition, Scientific American Books, NY.*

Transforming Nucleic Acids into Plants.

Embodiments of the present invention pertain to the production of transgenic plants comprising the cloned nucleic acids, e.g., chromosome intervals, isolated ORFs, and cDNAs associated with QTLs, of the invention. Techniques for transforming plant cells with nucleic acids are generally available and can be adapted to the invention by the use of nucleic acids encoding or corresponding to QTL, QTL homologs, isolated chromosome intervals, and the like. In addition to Berger, Ausubel and Sambrook, useful general references for plant cell cloning, culture and regeneration include Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) *Plant Molecular Biology* Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid acids of the present invention can be introduced into plants according to any of a variety of techniques known in the art. Techniques for transforming a wide variety of higher plant species are well known and described in the technical, scientific, and patent literature. See, for example, Weising et al. (1988) *Ann. Rev. Genet.* 22:421-477.

The DNA constructs of the invention, for example plasmids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology*, Volume 49 Humana Press Towata N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example Horsch, et al. (1984) *Science* 233:496; and Fraley et al. (1984) *Proc. Nat'l. Acad. Sci. USA* 80:4803 and recently reviewed in Hansen and Chilton (1998) *Current Topics in Microbiology* 240:22 and Das (1998) *Subcellular Biochemistry* 29: *Plant Microbe Interactions* pp 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: *DNA Cloning*, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (*U.S.A.*) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Preferred plants for the transformation and expression of *Sclerotinia* resistance associated QTL and other nucleic acids identified and cloned according to the present invention include agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower).

Additionally, preferred targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others.

Common crop plants which are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant, and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters).

Examples of tissue-specific promoters under developmental control include promoters that initiate transcription only in certain tissues, such as fruit, seeds, or flowers.

Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella et al. (1983), *Nature,* 303: 209. Viral promoters include the 35S and 19S RNA promoters of cauliflower mosaic virus. See, Odell et al. (1985) *Nature,* 313:810. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide, including those encoded by QTL or other nucleic acids correlating with phenotypic traits of the present invention, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops which encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

High Throughput Screening

In one aspect of the invention, the determination of genetic marker alleles is performed by high throughput screening. High throughput screening involves providing a library of genetic markers, e.g., RFLPs, AFLPs, isozymes, specific alleles and variable sequences, including SSR. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 324-, or a 1524-well format or in a matrix on a silicon chip or other format.

In one commonly used format, a dot blot apparatus is used to deposit samples of fragmented and denatured genomic DNA on a nylon or nitrocellulose membrane. After cross-linking the nucleic acid to the membrane, either through exposure to ultra-violet light or by heat, the membrane is incubated with a labeled hybridization probe. The labels are incorporated into the nucleic acid probes by any of a number of means well-known in the art. The membranes are washed to remove non-hybridized probes and the association of the label with the target nucleic acid sequence is determined.

A number of well-known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes are synthesized on a solid support. Using chip masking technologies and photoprotective chemistry, it is possible to generate ordered arrays of nucleic acid probes. These arrays, which are known, e.g., as "DNA chips" or as very large scale immobilized polymer arrays (VLSIPS™ arrays) can include millions of defined probe regions on a substrate having an area of about 1 cm$^2$ to several cm$^2$.

In another embodiment, capillary electrophoresis is used to analyze polymorphism. This technique works best when the polymorphism is based on size, for example, AFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The AFLP or SSR samples are loaded onto the capillary tube and electorphoresed. Because of the small amount of sample and separation matrix required by capillary electrophoresis, the run times are very short. The molecular sizes and therefore, the number of nucleotides present in the nucleic acid sample is determined by techniques described herein. In a high throughput format, many capillary tubes are placed in a capillary electrophoresis apparatus. The samples are loaded onto the tubes and electrophoresis of the samples is run simultaneously. See, Mathies and Huang, (1992) Nature 359:167.

Integrated Systems

Because of the great number of possible combinations present in one array, in one aspect of the invention, an integrated system such as a computer, software corresponding to the statistical models of the invention, and data sets corresponding to genetic markers and phenotypic values, facilitates mapping of phenotypic traits, including QTLs. The phrase "integrated system" in the context of this invention refers to a system in which data entering a computer corresponds to physical objects or processes external to the computer, e.g., nucleic acid sequence hybridization, and a process that, within a computer, causes a physical transformation of the input signals to different output signals. In other words, the input data, e.g., hybridization on a specific region of an array is transformed to output data, e.g., the identification of the sequence hybridized. The process within the computer is a set of instructions, or "program," by which positive hybridization signals are recognized by the integrated system and attributed to individual samples as a genotype. Additional programs correlate the genotype, and more particularly in the methods of the invention, the haplotype, of individual samples with phenotypic values, e.g., using the HAPLO-IM$^+$, HAPLO-MQM, and/or HAPLO-MQM$^+$ models of the invention. For example, the programs JoinMap® and MapQTL® are particularly suited to this type of analysis and can be extended to include the HAPLO-IM$^+$, HAPLO-MQM, and/or HAPLO-MQM$^+$ models of the invention. In addition there are numerous e.g., C/C++ programs for computing, Delphi and/or Java programs for GUI interfaces, and Active X applications (e.g., Olectra Chart and True WevChart) for charting tools. Other useful software tools in the context of the integrated systems of the invention include statistical packages such as SAS, Genstat, and S-Plus. Furthermore additional programming languages such as Fortran and the like are also suitably employed in the integrated systems of the invention.

In one aspect, the invention provides an integrated system comprising a computer or computer readable medium comprising a database with at least one data set that corresponds to genotypes for genetic markers. The system also includes a user interface allowing a user to selectively view one or more databases. In addition, standard text manipulation software such as word processing software (e.g., Microsoft Word™ or Corel Wordperfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system.

Integrated systems for genetic marker analysis of the present invention typically include a digital computer with one or more of high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to a label. The data so derived is then correlated with phenotypic values using the statistical models of the present invention, to determine the correspondence between phenotype and genotype(s) for genetic markers, thereby, assigning chromosomal locations.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, LINUX, or UNIX based (e.g., SUN™ work station) computers.

EXAMPLES

The following experimental methods and results provide additional details regarding specific aspects of protocols and procedures relevant to the practice of the present invention. The examples, which are provided without limitation to illustrate the claimed invention, involve the application of protocols well-known to those of skill in the art, and detailed in the references cited herein.

Mapping Population

A population of 264 recombinant inbred lines (RIL) was derived by single-seed-descent inbreeding from the $F_2$ to the $F_{6:7}$ generation between a parental line resistant ($P^R$) to *Sclerotinia* stem rot and a parental line susceptible ($P^S$) to *Sclerotinia* stem rot.

Molecular Marker Analysis

DNA Isolation.

Soybean DNA was extracted using a variation of the CTAB method (Murray and Thompson (1980) *Nucl Acid Res* 8:4321-4325; Keim et al. (1988) *Soybean Genet Newslett* 15:150-152), with the following modifications: lyophilized tissue (750 mg) was powdered by adding 2.5 g glass beads in a 50-ml tube and shaking in a paint-can shaker. The concentration of CTAB (hexadecyltrimethyl-ammonium bromide) in the extraction and precipitation buffers was reduced from 1% to 0.5%. After precipitation of the DNA with CTAB, the DNA pellet was dissolved in 2 ml 1 M NaCl by shaking at 65° C., 200 rpm, for approximately 2-3 h. The DNA was re-precipitated by adding 4.5 ml ice-cold 95% ethanol. The precipitated DNA was then washed with 1 ml of 65% ethanol, and again with 1 ml of 85% ethanol, to further remove salts. After the ethanol washes, the DNA was dissolved in Tris-EDTA buffer (10 mM:1 mM) at a concentration of 500 ng/μl, and stored at −20° C.

Restriction Fragment Length Polymorphism (RFLP) Analysis.

Most of the RFLP markers utilized were from PstI-cloned genomic libraries, and were either public (Keim and Shoemaker (1988) *Soybean Genet Newslett* 15:147-148) or proprietary to Pioneer Hi-Bred Intl., Inc. (denoted by the prefix: PHP). Some RFLP markers corresponded to USDA-ARS (Beltsville, Md.) cDNA clones (prefixed pBLT). The cloned inserts used as probes were amplified by the polymerase chain reaction with T3 and T7 primers. The restriction enzymes EcoRI, HindIII, EcoRV, DraI, TaqI, and HaeIII were used to digest soybean parental and population DNA. Restriction enzyme digestion of DNA, electrophoresis, Southern transfers (blotting), and DNA hybridization were all performed as described previously (Keim et al. (1989) *Theor Appl Genet* 77:786-792).

Amplified Fragment Length Polymorphism (AFLP) Analysis.

The KeyGene protocol was used in the AFLP amplification with the following modifications. Briefly, DNA was digested with EcoRI/MseI restriction enzymes and ligated to EcoRI and MseI adaptors. The restriction ligation (RL) products were diluted 1/10 for use in the Plus 1 reaction. The Plus 1 reactions contained 5.0 μl of the diluted RL products, 1.5 μl each of the Mse+1 primer and Eco+1 primer (50 ng/μl), 0.4 μl of a mixture of dNTP's (25 mM), 5.01 of 10× high magnesium Hot Tub buffer, 0.2 μl Hot Tub polymerase (3 units/μl), and 36.4 μl of $H_2O$ for a final volume of 50.0 μl. The Plus 1 amplification used twenty cycles of 94° C. (30 sec.), 56° C. (1 min.), and 72° C. (1 min.). The Plus 1 products were diluted 1/20 for use in the Plus 3 reactions. The Plus 3 reactions contained 5.0 μl of the diluted Plus 1 products, 0.6 μl of the Mse+3 primer and 0.5 μl $\gamma^{33}$P-ATP labeled Eco+3 primer (10 ng/μl), 0.2 μl of a mixture of dNTP's (25 mM), 2.0 μl of 10× high magnesium Hot Tub buffer, 0.1 μl Hot Tub polymerase (3 units/μl), and 11.5 g of HPLC $H_2O$ for a final volume of 20.0 μl. The Plus 3 amplifications used a 94° C. (2 min.), followed by 13 cycles of 94° C. (30 sec.), 65° C. (30 sec., decrease annealing temp by 0.7° C. each cycle), and 72° C. (1 min.) followed by 23 cycles of 94° C. (30 sec.), 56° C. (30 sec.), and 72° C. (1 min.), and followed by 72° C. (2 min.) step. The Plus 1 and Plus 3 reactions differ form the reactions in KeyGene's protocol in the use of Hot Tub polymerase instead of Taq polymerase. The Plus 3 products were loaded to polyacrylamide gels (4.5% acrylamide, 7 M urea, 0.5× TBE), and the gel was run for 3 hours at a setting of 45° C., 120 Watts. The labeled products separated on the Plus 3 gels were detected using a phospho-imaging system.

Simple Sequence Repeat (SSR) Analysis.

SSR markers used were developed by either public sources (Cregan et al. (1994) *Meth Mol Cell Biol* 5:49-61) or by DuPont. Amplification by PCR was performed in 10 μl reaction volume containing 10 ng of genomic DNA, 1× reaction buffer, 1.5 mM $MgCl_2$, 0.2 mM dNTP, 0.34 μM of forward and reverse primers, and 0.5 units of AmpliTag DNA polymerase (Perkin-Elmer Cetus, Norwalk, Conn.). The SSR PCR products were analyzed either by size separation on 2% metaphor gel and visualized by ethidium bromide staining, or by sequencing on an automated ABI 377 sequencer using GeneScan software.

Sclerotinia Screening

Inoculum Source.

Sclerotia from infected greenhouse plants were stored in culture tubes in a 45° C. refrigerator. Six days before plant inoculation, sclerotia were plated on potato dextrose agar (PDA) media and placed in a 25-27° C. incubator. After 4 days, a single plate with uniform mycelial growth extending to at least 1½ inches in diameter was used. Plugs were cut in 4 mm square from the edge of the mycelia and were plated in the center of PDA plates. Plates were put back in the 25-27° C. incubator for 24 hrs.

Carrot Preparation.

Large fresh carrots were rinsed in distilled water and peeled. Carrots were cut into 5-10 cm sections and then pushed lengthwise through a Zyliss brand French frier. The resulting 8 mm square lengths were cut into approximately 2 mm thick pieces. Carrot pieces were placed in an autoclave bag and autoclaved for 1½ to 2 minutes.

Carrot Inoculation.

Autoclaved carrot pieces were placed on the edge of the growing mycelia that had incubated for 24 hrs. Eight to twelve pieces were placed on each plate, depending on the mycelial diameter. Each carrot piece was placed with its outer edge positioned on the growing edge of the mycelia. Plates were returned to incubator for 22-24 hrs.

Stem Inoculation.

Plants were inoculated between V3 and V4 stages. Each inoculated carrot piece was placed on a 2 inch square parafilm just at the tip of the center slit. The carrot piece on the parafilm was positioned on the stem internode just above the petiole immediately below the last fully developed leaf. The parafilm was wrapped around the stem with the center cut positioned downward. The carrot piece was pulled into contact with the stem while wrapping the parafilm.

Plant Incubation and Removal of Inoculum.

Inoculated plants were placed on a shaded bench where a humidifier runs continually. The humidity in the room was set at 70%. Plants stayed in this humidity chamber for 48 hrs. Inoculum was removed form stem inoculated plants by taking off parafilm and pulling carrot pieces off. Paper tissues were used to wipe the plant stem of remaining inoculum.

Disease Scoring.

Plants were rated for disease severity 6-8 days after inoculation. Plants were rated on a scale of 1 to 9, with 1 being stem girdled and having large lesion, 3 being stem girdled, 5 being larger lesion in length, 7 being small lesion and black margin, and 9 being no infection or browning. The final score for each RIL was an average of two replications and expressed as the percentage of the $P^R$ score.

Genetic Mapping

Genetic mapping and QTL analysis were performed using MapManager QTb27 (Manly (1993) *Mamm Genome* 1:123-126; Manly and Olson (1999) *Mamm Genome* 10:327-334). The Kosambi centiMorgan function was used. A QTL was declared if its Likelihood Ratio Statistic (LRS) exceeds the threshold of 12.3. The threshold was established by performing 500 permutation tests. Composite Interval Mapping (CIM) were also performed by adding background loci (usual the loci with the largest effect) to simple interval mapping (SIM).

QTL Mapping

Genetic Mapping

Genetic mapping has placed 333 molecular markers to 20 linkage groups (Lg) that are corresponding to 20 soybean chromosomes and public linkage group nomenclature. Of 331 markers, 53 are RFLP, 159 are AFLP, 21 DuPont SSR and 100 public SSR. The linkage map covers ~2400 cM.

QTL Mapping

QTL analysis for stem inoculation data identified 7 QTL responsible for white mold resistance. The QTL with larger effects on white mold locate on soybean Lg A1, D2, and L. With Composite Interval Mapping, the QTL on Lg A2, B2 and D2 show additive effects, and these three QTL together explain 42% of total variation.

Specific Linkage Groups

QTL on Lg A1

This QTL has LRS of 19.0 and explains 14.0% of the total variation. The favorable allele (allele which is resistant to *Sclerotinia* stem rot) of this QTL comes from $P^S$. The QTL is in the interval of Satt155—SLS1C.L24 with a distance of 1.3 cM. It is interesting that SLS1C.L24 is a homolog to Berberine-bridge forming enzyme (BBE). The BBE [9S0-reticuline:oxygen oxidoreductase (methylene-bridge-forming), EC 1.5.3.9] is a key covalently flavinylated oxidase in the benzophenanthridine alkaloid biosynthesis in plants (Kutchan and Dittrich (1995) *J Biol Chem* 270:24475-24481; Blechert et al. (1992) *Proc Natl Acad Sci USA* 92:4099-4105; Dittrich and Kutchan (1991) *Proc Natl Acad Sci USA* 88:9969-9973; Chou and Kutchan (1998) *The Plant J* 15:289-300). The alkaloid families have pharmacological activities. Berbrine, for example, is currently used as an antibacterial treatment for eye infection in Europe and for intestinal infections in the Far East. The benzophenanthridine alkaloid sanguinarine is an antimicrobial used in the treatment of periodontal disease in both the United States and Europe (Kutchan and Dittrich (1995) *J Biol Chem* 270:24475-24481). In addition, BBE has anti-phytophthora and anti-Pythium activity, and carbohydrate oxidase activity (Stuiver et al. (1998) WO 98/13478). The BBE-transgenic plants may have enhanced resistance to pathogens (Stuiver et al., 1998). BBE and several other enzymes in the pathway were induced by elicitors in California poppy (Blechert et al. (1992) *Proc Natl Acad Sci USA* 92:4099-4105; Dittrich and Kutchan (1991) *Proc Natl Acad Sci USA* 88:9969-9973). The benzophenanthridine alkaloids accumulated in the suspension cells of plants in response to the addition of elicitors (Schumacher et al. (1987) *Plant Cell Rep* 6:410-413; Cline and Coscia (1988) *Plant Physiol* 86:0161-0165; Eilert et al. (1984) *J. Plant Physiol* 119:65-76). The alkaloid pathways may also be regulated by octadecanoic-derived components and jasmonic acid (Blechert et al. (1992) *Proc Natl Acad Sci USA* 92:4099-4105; Kutchan (1993) *J. Plant Physiol* 142: 502-505; Facchini et al. (1996) *Plant Physiol* 111:687-697). It is not known if the benzophenanthridine alkaloid biosynthesis pathway exists in soybean, but its potential antifungal activity and carbohydrate oxidase activity imply that it could be involved in *Sclerotinia* stem rot resistance.

QTL on Lg A2

This QTL has LRS of 19.3 and explains 12.0% of the total variation. The favorable allele of this QTL comes from $P^S$. The support interval of this QTL is Satt129-Satt329 of 31.7 cM.

QTL on Lg B2

This QTL has LRS of 18.9 and explains 12.0% of the total variation. The favorable allele of this QTL comes from $P^R$. The support interval of this QTL is Satt556 and P1694 of 12.7 cM.

QTL on Lg D2

The QTL is in the interval of PHP8701R-Satt311 of 14.5 cM. This QTL explains 14.0% of the total variation with LRS of 26.6. The favorable allele of this QTL comes from $P^R$.

QTL on Lg E

The support interval for this QTL is the PHP100771-PHP82410 with the genetic distance of 30.8 cM. The peak interval is in the PHP10118C-Satt231 of 18.8 cM. This QTL has a LRS of 24.0, and explains 10% of the total phenotypic variation. The favorable allele of this QTL attributed to $P^S$.

QTL on Lg J

The QTL is in the interval of P1047-A724_1 of 22.5 cM. The QTL explains 6% of phenotypic variation with the LRS of 13.6.

QTL on Lg L

This QTL is in the interval of Satt523 and SLS2C.F20 with the distance of 11.7 cM. This QTL explains 16.0% of the variation with the LRS of 26.1. Interestingly, SLS2C.F20 is an EST coding for pathogenisis-related protein 1 (PR1). The significance of PR 1 proteins lies in the fact that they show strong antifungal and other antimicrobial activity. Alexander et al. (1993) *Proc Natl Acad Sci USA* 90:7327-7331, reported that transgenic *N. tabacum* cv *Xanthi nc*, which constitutively produce PR-1a protein, showed an increased tolerance to two oomycete pathogens. Niderman et al. (1995) *Plant Physiol*

108:17-27, tested the antifungal activity of purified tobacco and tomato PR-1 proteins against Phythopthora infestans. The basic PR-1 proteins (PR-1g (tobacco) and P14C (tomato), found to be most effective in the assays. Therefore, there is a possibility that The EST, SLS2C.F20, is involved in the *Sclerotinia* stem rot resistance.

Table 2 summarizes the chromosome intervals, and subintervals defined by the flanking markers associated with *Sclerotinia* stem rot resistance. Subintervals are not given for linkage group A1 because it is already tightly defined to a region of 1.3 cM. Due to asymmetry of an LRS peak within an interval, subinterval boundaries that fall outside the defined interval have been given a distance of 0 cM from the interval boundary, see, e.g., linkage group B2.

TABLE 2

Summary of Linkage Intervals

| Linkage group | Defined chromosome interval | Sub-interval | Distance to flanking markers |
|---|---|---|---|
| A1 | 1.3 cM flanked by Satt155 and SLS1C.L24 | N/A | N/A |
| A2 | 31.7 cM flanked by Sat_129 and Satt329 | 95% | 7 cM to Sat_129 16 cM to Satt329 |
|  |  | 90% | 5 cM to Sat_129 14 cM to Satt329 |
|  |  | 80% | 1 cm to Sat_129 11 cM to Satt329 |
| B2 | 12.7 cM flanked by Satt556 and P1694 | 95% | 0 cM to Satt556 9 cM to P1694 |
|  |  | 90% | 0 cM to Satt556 9 cM to P1694 |
| D2 | 14.5 cM flanked by PHP8701R and Satt311 | 95% | 0 cM to P8701R 10 cM to Satt311 |
|  |  | 90% | 0 cM to P8701R 8 cM to Satt311 |
| E | 18.8 cM flanked by PHP10118C and Satt231 | 95% | 7 cM to P10118C 2 cM to Satt231 |
|  |  | 90% | 6 cM to P10118C 1 cM to Satt231 |
| J | 22.5 cM flanked by P1047 and A724_1 | 95% | 4 cM to P1047 15 cM to A724_1 |
|  |  | 90% | 4 cM to P1047 14 cM to A724_1 |
| L | 11.7 cM flanked by Satt523 and SLS2C.F20 | 95% | 2 cM to Satt523 4 cM to SLS2C.F20 |
|  |  | 90% | 1 cM to Satt523 3 cM to SLS2C.F20 |

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

SEQUENCE LISTINGS

SEQ ID NO: 1 (SLS1C.L24)
ganagcgctggagctccaccgcggtggcggccgctctagaactag
tggatccccgggctgcaggaattcggcacgagGAGGGTCTCTCC
TACGTTGCCAAGGATCCATTTGTCGTCCTTGACCTCATAAACCTT
CGAAAAATCGAAGTGGACGCAGAAAACAGCACTGCATGGTTCTA GCTGGTGCAACCATTGGTGAACTTTACTACAGCATTAGCCAGAAA
AGCANAACACTAGGGTTTCCAGCAGGTGTGTGCCCCCCTGTGGGA
ACTGGTGGCCATTTCAGTGGTGGTGGCTATGGATTCTTGATGCGT
AAGTTCGGTCTTGCTGCTGATAATGTGATTGATGCTCACATACTT
GATGTGAANGGTAATCTTCTTGATANAGAAGCCATGGGTGAGGAT
CTGTTTTGGGCCATTATNAGGAGGTGGGGGAGCAANCTTTGGAGT
CATCGTGGCTTGGNAGATANAACNTGTTTCAGTTCCATCAACTGT
GACAGTGTTTAGGGGTTCCAAGGACATTGGGACAAAATGCAACCG
AGATTGTTCATAAGNGGGAACCTNGTGGNGAATAAACTTGNGGG SEQ ID NO: 2 (SLS2C.F20)
gctctagaactagtggatccccgggctgcaggaattcggcacca
gATTAAGCATAATTAATATAATGGGGTACATGTGCATTAAGATTT
CGTTTTGTGTGATGTGTGTGCTGGGGTTGGTGATCGTGGGTGATG
TTGCCTACGCTCAAGATTCAGCAGAAGACTACGTGAATGCACACA
ATGCAGCACGAGCAGAGGTGGGTTCTCAATCACCAAGACAAACAG
TGATTGTTCCAAGTTTGGCTTGGGATGATACGGTTGCTGCTTATG
CAGAGAGCTATGCTAATCAACGCAAAGGTGACTGCCAACTGATCC
ACTCTGGTGGTGAATACGGAGAGAATATTGCAATGAGCACTGGTG
AACTAAGTGGCACAGATGCAGTGAAAATGTGGGTTGATGAGAAAT
CCAACTATGACTATGATTCTAACTCTTGTGTTGGAGGAGAGTGCC
TGCACTACACACAGGTCCGTTTGGGCTAACTCGGTGCGTCTTGGA
TGTGCCAAAGTGACATGTGATAA SEQ ID NO: 3 (PHP8701R)
CACAGTCACAGCTTAATGGCGGAGGAAGAAGTTGCGGCACCCGCT
GCCAGCCCCGTTCCCCCTGATAACAAACGCAAGCTCGAAGATCTG
CAACCCGAAAACGCCGAATCTAATGCCAACTCCATCTCCGACGCC
GTGAACGCCGATGACGCCGCCGTTTCCGCCGAGACCGAGAACAAG
CGTCTCCGCCTCGACGACCACCAGGATGGCCTCGGTACCGTTTTT
GTCAATCTCAACTATTCGTGGTTTTGCAATGCTCGTAATAATAAT
TTATTTCATTCACTATTAGTATATAAATCCTTGAGGATGATATAG
GCTTTAGGCAA SEQ ID NO: 24 (SATT155)
TTAACATCGTATATATGGATTGCTTATGTGCAATGGCAGATCCAA
CACCTGGCCTAATTGGGGAATTTATTTTTAAAAAATATTATTATT
ATTATTATTATTATTATTATTATTATTATTATTATTATTATTATT
ATTAAAACAAAAATTAAAATTAACCACAGTGAGCTAAAAATGGAA
TGAATTGTGCAGCAAAATAAATTATAAAATTACTTAATGAAATGA
AAAAAGTAAAACTTAAGAAAAAAAAAAGCTAGTGATAAAAAATT
AGGAGTTGTG SEQ ID NO: 25 (SAT_129)
TTTAGCGTGGAATTAAGTTTAAACTTAGGTTAAAAGAGAATAACT
TAAATTAATATTCTCAAATTTAGATATTAAAAATATAATTTCTTT
AAATTTGGATTAAAGAAAATTTGTGGNTCTTAGTTATTTGATAGT
TTGACCTTATTTCAGTACAAGTCGGGTGAATAATAATAATAATAA
TAATAATAATAATAATAATAATAATAATAATAATAATAATAATAA
TAATAATAATAATAGAACCAACCTTTTTCTTTTGCCAAGAAAAAT
AATACCTTAAGTCCCGAACATGTGAAGATAACTCACAATTCTTAC
RCGGTTTCTAACTGATACCTCCTCCACCCGACGATATTGCTAGAA
ACGAGAATTTATAAACTTATGAAAATTTTATCATTAAATTAAATA
ATATCACTCTTTAAAATTAAATTTTGTATCAAACAATTGACATAT
CTCATTTGATTTTCAGATCATTATGCTAAGCGCTTCANCAAATAA
ATTATCCAGATTGAAAGAGCAGGCCGAGGAATACGCAGCTCTGAT
CATGGAAGAGTTAGACCCTGAAAGACTTCGCTACAT SEQ ID NO: 26 (SATT329)
CCGTGTTATGTCGTCNTTGGGTCAAATTGGGTGCCATGATTATGA
CCAATAGCTTGGCTTTCATTCAGAGTGCCTTGACTGAGCATTATC
AGTAGCATGCCTTCTACCATTAAGTCACTCGAACCAGTTGCAAGT
AGTTGGTCTCTACAACGAAAAATGAAGAACCATGAACGACGAAAA
ATGAAGAAAAATAGAACCACTAAGAACGAAAAATGGAACCAACAA
CAACACTTACAGCCCAGTTTCGAAATCCTTTAAATAGAGAAAATA
ATATCACTATTATAATTTAGGAATGTTCATGGTTATCAATTACTC
ACGAACTTGAATGGACGCAAAATTGGATTTAGTATTTTTTGCATT
GAATCAAATCTTATCTAATTCTTTNCAANCCATNGATTTTNGGGT
GNANTCACATATTTTTATNTGTCTANATATTATTATTATTATTAT
TATTATTATTATTATTATTATTATTATTATTATTATTATTATTAT
TATTATTAAATTTTTTAATATCAATTACTATTACTATCATAACT
TAGTAAAAGTGACATTATCTTCTTTTTTTTTTCAGTTCTCACGTT
TTATTCGGTTACTTTTACGAAGATTAGGATTTTAACTGCCATTTG
ATTTTAAAAATATCTCTTTTAATTTTTAATTAATTTATTTCAAAC
TATTTTAGATTTAGTTAAAGTTTTATTTGTATTACTCATTTAACT
ATTAGAGAACATTAGAATTTTCAAAATGCTCTAATAGTTTTAGTT
TTTTAAGGCTCCGTGAGTGTGGTGATTAAATTTATTTATTATATT
TCAAATTTTTAAATCATGTTTAATATAATTTCATTTAGTTTCAAAT

SEQUENCE LISTINGS

ATAAGCAACAAAATCCCTTACTTTTGGGTCTCAAATATAAATAAA
TTTTAATTACTTATGTCTTATTTAATGAAACTCTCTCAAAAATAT
CATTTTTTAATGAGGTCAAAGACTTTTTTATGTTTGAT

SEQ ID NO: 27 (SATT556)
TCCCATTGCTTCGGGCCACAAGTCTACGACTATAATAATTCGCCA
AACAGAGTGTACCCAATATTTTTCAAAAGCAAACAACACAGAAGA
ATCACCACACATAACAAGCAATCATAACCCAGATACAGACAATAA
AACCCGATAAATAAGATTTCATGAATAATAATAATAATAATAATA
ATAATAATAATAATAATACTCAAAGACCAAAATTTCATTTTC
GAAACATGTATATAGGCTTCAGAGATGAACGAACATAAAATACATA
AGAAAACAAGGTGCACAATTAGG

SEQ ID NO: 28 (SATT063: closest public marker to
P1694)
AAAATTATAANTATAATAATGAAAATGATTAACAATGTTTATGAT
AATTATACATATTATATTTTTACTGCATAGGTATTATTATTATT
ATTATNATTATTATTATTATTATTATTATTATTATTATTATTATT
ATTAAACTAATTGTTATTAACTGATGCAAGTAATAAAAAACTAN
NNATCAGCGATGAANATGAAANTGCTAAAAATATTNNATACACAA
CTGTGANNAGGTNAGATGTAANTGNGGCNCCCTNANTGNGCTCAA
TGTGTAATTGNGGTCTNCTATTCCAAGANAGAGACANGNGGTCCN
TCTANNTCAGAAAAANNCANAATNGNGGNCCTCCATATTTATAAA
ANGTGTAACCCNGCGGGNCANCNTCCACCNCNATCTANGCCNCNTC
NCTTNNATTNCTCACATANTAACNAACCNACCNCTCCNCGCTGNT
ACTTN SEQ ID NO: 29 (SATT311)
ACAAAGAATTCATTTTCCTCCATTACTTGGTCTATTTTCATCTTC
AATTCAGTGTTTTTCACTTCTAACATGACATTCTTCTTTGTTATA
TCATCCTGCTAATCAAAGAAGCTAATTTTATATGTAATGAATTAA
TGTGGAGTAGAAAAGATAAAGATCAATAATCTATGACAAGACCGA
AAAGATTGAGGTAAAATAAAATCTCACATGATAAAAGCTCAACTT
AGGGGGGAACCACAAAAATCTTAATCAAACAAACCACAAAAAGATG
AAACAAAATAGTAATAGTAATATAATATAACAATGCCACATATAT
ATTATACTAATAACAATAATAATAATAATAATAATAATAATAAT
AATAATAATATATGTAGTAGTGAATTCATCACAGCCTGAGCTTCA
ACTTACAACTACTGCTAGAAATTCTAATATCATTACTAGCACCAA
GATTATCCACCTCAAGCCTACACCTAACCCTGAACTTGACTTTGA
AGAGCTTCAGCTTACCAAGCTTAACTCTCACAGGCTAATTCACCT
TAAGATTGAGAGGAACATTGTTGGTCTGTTGCAACTACTCCTGAA
TTCTATTGACCAAACCACTTGCATCATGTGCTTGACCAGTTAGAG
GCAAATCAAGCACTGTTGTGTTCCTATGACCCTGGTAGAACTTTG
GCAAGGACCCTTCACACA SEQ ID NO: 30 (SAT_124: closest public marker to
PHP10118C)
GGATCCATTCCACTTTTTGTACAATATTTTATGCATTAAATACTT
AGAATTATATACATAATAACAGTATATTTATATATATATATATA
TATATATATATATATATATATATATATATATATATATATATATAT
ATATATATTGACAGACCTATATGCGTTAGAGGTGGATAAATGTAT
CTCTTTATTTTAATAAAATTACATATATTTATCTTAAAATATAT
AATTTATACCACTAATGGATGTTTGAACTTGTTATTGTTAGAACA
AATCTCTTTTAACCTGTGATATTACAAACTACAAAGAAACACGGG

TTATTAATAAAATGCGAAAATTACAGATCAAAACATACCTCCAGC
CATTGCTATGAAGA

SEQ ID NO: 31 (SATT231)
TTATTGTTTTTTATACTGTTATATGTGCAAAATGTTCATCATCTT
TTTCTGATCCCTAATTTCTGCTTGTGAAACTGGCTGATTATTTTT
TATTAGAAATTAGAAATAAATGCACTTTAATAATAATAATAATAA
TAATAATAATAATAATAATAATAATAATAATAATAATAATAATAA
TAATAATAATAATAATAATAATAATAATAATAGTAATCTGTG
ATGGGAACAGAAGGAAGTTTTGATGTTGATTCGTGGCCTTTTTTT
TCTTTTCATTTTTTGTCTAATTTTTAAATGAGTTACTTTTGCATG
TTTTTTCTTCTCCGCTAATTTTGGTGTGGTAGATTCCTGATGTCT
GTTAGAGATTTTTTTGGGGAATAAGAATAATATTTATCTGTTTTC
CTCTCCTGTTGTTTAATTTTCCTATGCTTTTTTATGACTAGGTTG
TAACTTTTATTTATTTATTANNTTGACAAGGTNTCAACTTTATTC
TGTTTGATTTGAATCCGATTCTGGATTTTTATNC

SEQ ID NO: 32 (SATT596: closest public marker to
P1047)
GAACTCTGGTCCATCCCTTCGTCCACCAAATATTCAAATGTTCCT
TTTTAGGGTTATCTTTTTCCTTCCACCATTTTTAACATCTCTTTC
TCCTTTGCATTATTATTATTATTATTATTATTATTATTATTATTA
TTATTATTATTAACCTATACCTANAACAATCCTCTATTTTAA
TTAAATAATCCCNCTTAGTATTCATGTCTCTCTCTCTATAGGAAA
CTTTACACTCGTATGATTACTATCTTGTACGGAATCGACGGGTAG
TCGACACTTGTTAACTGACTATCACTTTACACATATTATTATTGT
GAACAATTATCAACTCGGTCACTATCATCTTTTATAAGACAAAAG
ACCATGTAAGAATAGGAAAGTCATATTTTGTTTACAATATACACC
TTAGACAAATATCTATATCCTTTATACAAACAAGGCTCTAACACA
TGCAGAAAGTACCAAAATGCCCCTAACTTTCTGAGGTGTCGTCGT
CTGGGGATTTTGTTCCTGCCCAAAATGGTTCGTGTGGGTTTTTA
GAATTCTTATGGAATTGGGATACGTGGTACGCGTACACGCGTTT
TGGTGG SEQ ID NO: 33 (SATT523)
GGGTCAACAAAAGTTGATCATGAAATTGTGGAGCTCATTTCGGCC
AAGAAAATTAATCAACTCCAGTTAAACTTGTGTTTATCCTATAAA
TTGTAAATTATTGCTTATCATGCTTATTGAAAAAATTACATGAT
TATCTCAATGTACTGTACATTTTTATTGTAAATTTTTTATGTTA
TATTATATAGTGACACGTTTTGATATAGCTAATTTCTTCCTTGA
GAATTTTCTGCTGTAAATTTAATTGATAAAATAATAGAAAGACTT
TTTTAAAGAAATTTAATAATAATAATAATAATAATAATAATAATAA
ATAATAATAATAAGTTCTATTATTTGCGAATAAAGTTAAAAATAA
CAGCCGAAAAGTTCAACAAATTTACAACTTTTGCATGTGAAAGC
TACAACTTCAATTTTTCTTTTATGTAAGTCACTAAACTTACATAT
ATTTAACAAATTTTTGCAAATATATCTTGCATAAGTAAATTATAAA
ATAAATTTGGTTTACATGTGTTTATTAGAATAAAAATTTAAAATT
AATATAATTAAATTATATTTTTATATAAAGAATGGATCAAAATTA
AATTTATATTTTTATAAGTAGAGTGCTTTTATTTAAATATACATA
CTTTGTCAGAATGTATATGGCTACACTTCGTAAACAGACAAACTA
GCACACGGTCACATATTTTTCAATTCAAAATTGTGACGATGAAGA
ATAAAGTATCAA

What is claimed is:

1. A method of identifying a *Sclerotinia* stem rot resistant soybean by identifying a quantitative trait locus ("QTL") associated with *Sclerotinia* stem rot resistance, the method comprising:
   (i) detecting at least one nucleic acid from the soybean, wherein the nucleic acid localizes to a chromosome interval flanked by and including a marker pair selected from:
      a) Sat_129 and Satt329, and
      b) Satt556 and P1694; and,
   (ii) identifying the soybean comprising the nucleic acid, thereby identifying the *Sclerotinia* stem rot resistant soybean.

2. The method of claim 1, wherein the detecting of step (i) comprises detecting at least two nucleic acids, wherein the nucleic acids localize to different chromosome intervals, wherein the chromosome intervals are:
   a) an interval flanked by and including the marker pair Sat_129 and Satt329, and
   b) an interval flanked by and including the marker pair Satt556 and P1694.

3. The method of claim 1, wherein the at least one nucleic acid detected in step (i) comprises a marker selected from the group consisting of Sat_129, Satt329, Satt556 and P1694.

4. The method of claim 1, wherein the soybean is a whole plant, a plant organ, a plant seed, or a plant cell.

5. The method of claim 1, wherein the identified soybean or a progeny thereof is crossed with a second soybean, and wherein the second soybean lacks the at least one nucleic acid detected in the identified soybean.

6. The method of claim 5, further comprising introgressing *Sclerotinia* stem rot resistance into at least one progeny soybean of the cross wherein the progeny plant comprises the at least one nucleic acid.

7. The method of claim 5, wherein the identified soybean or a progeny thereof and the second soybean are each a whole plant.

8. A method of identifying a *Sclerotinia* stem rot resistant soybean by identifying a quantitative trait locus ("QTL") associated with *Sclerotinia* stem rot resistance, the method comprising:
   (i) detecting at least one nucleic acid from the soybean, wherein the nucleic acid localizes to a chromosome interval flanked by and including the markers Sat_129 and Satt329, and
   (ii) identifying the soybean comprising the nucleic acid, thereby identifying the *Sclerotinia* stem rot resistant soybean.

9. A method of identifying a *Sclerotinia* stem rot resistant soybean by identifying a quantitative trait locus ("QTL") associated with *Sclerotinia* stem rot resistance, the method comprising:
   (i) detecting at least one nucleic acid from the soybean, wherein the nucleic acid localizes to a chromosome interval flanked by and including the markers Satt556 and P1694, and
   (ii) identifying the soybean comprising the nucleic acid, thereby identifying the *Scierotinia* stem rot resistant soybean.

* * * * *

SEQUENCE LISTING

<160> NUMBER OF SEQ ID NOS: 33

<210> SEQ ID NO 1
<211> LENGTH: 584
<212> TYPE: DNA
<213> ORGANISM: Glycine max
<220> FEATURE:
<221> NAME/KEY: misc_feature
<222> LOCATION: (3)..(3)
<223> OTHER INFORMATION: unknown (a,c,g or t)
<220> FEATURE:
<221> NAME/KEY: misc_feature
<222> LOCATION: (230)..(230)
<223> OTHER INFORMATION: unknown (a,c,g or t)
<220> FEATURE:
<221> NAME/KEY: misc_feature

```
<222> LOCATION: (369)..(369)
<223> OTHER INFORMATION: unknown (a,c,g or t)
<220> FEATURE:
<221> NAME/KEY: misc_feature
<222> LOCATION: (386)..(386)
<223> OTHER INFORMATION: unknown (a,c,g or t)
<220> FEATURE:
<221> NAME/KEY: misc_feature
<222> LOCATION: (423)..(423)
<223> OTHER INFORMATION: unknown (a,c,g or t)
<220> FEATURE:
<221> NAME/KEY: misc_feature
<222> LOCATION: (441)..(441)
<223> OTHER INFORMATION: unknown (a,c,g or t)
<220> FEATURE:
<221> NAME/KEY: misc_feature
<222> LOCATION: (464)..(464)
<223> OTHER INFORMATION: unknown (a,c,g or t)
<220> FEATURE:
<221> NAME/KEY: misc_feature
<222> LOCATION: (470)..(470)
<223> OTHER INFORMATION: unknown (a,c,g or t)
<220> FEATURE:
<221> NAME/KEY: misc_feature
<222> LOCATION: (474)..(474)
<223> OTHER INFORMATION: unknown (a,c,g or t)
<220> FEATURE:
<221> NAME/KEY: misc_feature
<222> LOCATION: (555)..(555)
<223> OTHER INFORMATION: unknown (a,c,g or t)
<220> FEATURE:
<221> NAME/KEY: misc_feature
<222> LOCATION: (564)..(564)
<223> OTHER INFORMATION: unknown (a,c,g or t)
<220> FEATURE:
<221> NAME/KEY: misc_feature
<222> LOCATION: (569)..(569)
<223> OTHER INFORMATION: unknown (a,c,g or t)
<220> FEATURE:
<221> NAME/KEY: misc_feature
<222> LOCATION: (581)..(581)
<223> OTHER INFORMATION: unknown (a,c,g or t)

<400> SEQUENCE: 1
ganagcgctg gagctccacc gcggtggcgg ccgctctaga actagtggat cccccgggct     60
gcaggaattc ggcacgagga gggtctctcc tacgttgcca aggatccatt tgtcgtcctt    120
gacctcataa accttcgaaa aatcgaagtg dacgcagaaa acagcactgc atgggttcta    180
gctggtgcaa ccattggtga actttactac agcattagcc agaaaagcan aacactaggg    240
tttccagcag gtgtgtgccc ccctgtggga actggtggcc atttcagtgg tggtggctat    300
ggattcttga tgcgtaagtt cggtcttgct gctgataatg tgattgatgc tcacatactt    360
gatgtgaang gtaatcttct tgatanagaa gccatgggtg aggatctgtt ttgggccatt    420
atnaggaggt gggggagcaa ncttrggagt catcgtggct tggnagatan aacntgtttc    480
agttccatca actgtgacag tgtttagggg ttccaaggac attgggacaa aatgcaaccg    540
agattgttca taagngggaa cctngtggng aataaacttg nggg                    584

<210> SEQ ID NO 2
<211> LENGTH: 518
<212> TYPE: DNA
<213> ORGANISM: Glycine max

<400> SEQUENCE: 2
gctctagaac tagtggatcc cccgggctgc aggaattcgg caccagatta agcataatta     60
atataatggg gtacatgtgc attaagattt cgttttgtgt gatgtgtgtg ctggggttgg    120
tgatcgtggg tgatgttgcc tacgctcaag attcagcaga agactacgtg aatgcacaca    180
atgcagcacg agcagaggtg ggttctcaat caccaagaca aacagtgatt gttccaagtt    240
```

```
tggcttggga tgatacggtt gctgcttatg cagagagcta tgctaatcaa cgcaaaggtg    300
actgccaact gatccactct ggtggtgaat acggagagaa tattgcaatg agcactggtg    360
aactaagtgg cacagatgca gtgaaaatgt gggttgatga gaaatccaac tatgactatg    420
attctaactc ttgtgttgga ggagagtgcc tgcactacac acaggtccgt ttgggctaac    480
tcggtgcgtc ttggatgtgc caaagtgaca tgtgataa                            518
```

```
<210> SEQ ID NO 3
<211> LENGTH: 326
<212> TYPE: DNA
<213> ORGANISM: Glycine max

<400> SEQUENCE: 3
cacagtcaca gcttaatggc ggaggaagaa gttgcggcac ccgctgccag ccccgttccc     60
cctgataaca aacgcaagct cgaagatctg caacccgaaa acgccgaatc taatgccaac    120
tccatctccg acgccgtgaa cgccgatgac gccgccgttt ccgccgagac cgagaacaag    180
cgtctccgcc tcgacgacca ccaggatggc ctcggtaccg tttttgtcaa tctcaactat    240
tcgtggtttt gcaatgctcg taataataat ttatttcatt cactattagt atataaatcc    300
ttgaggatga tataggcttt aggcaa                                         326
```

```
<210> SEQ ID NO 4
<211> LENGTH: 20
<212> TYPE: DNA
<213> ORGANISM: Artificial
<220> FEATURE:
<223> OTHER INFORMATION: synthetic oligonucleotide primer for
      amplification of P1694

<400> SEQUENCE: 4
tgtcaataaa tggctaatcg                                                 20
```

```
<210> SEQ ID NO 5
<211> LENGTH: 21
<212> TYPE: DNA
<213> ORGANISM: Artificial
<220> FEATURE:
<223> OTHER INFORMATION: synthetic oligonucleotide primer for
      amplification of P1694

<400> SEQUENCE: 5
tggtagtttt cacacgttat g                                               21
```

```
<210> SEQ ID NO 6
<211> LENGTH: 28
<212> TYPE: DNA
<213> ORGANISM: Artificial
<220> FEATURE:
<223> OTHER INFORMATION: synthetic oligonucleotide primer for
      amplification of Sat_129

<400> SEQUENCE: 6
ttcagtacaa gtcgggtgaa taataata                                        28
```

```
<210> SEQ ID NO 7
<211> LENGTH: 24
<212> TYPE: DNA
<213> ORGANISM: Artificial
<220> FEATURE:
<223> OTHER INFORMATION: synthetic oligonucleotide primer for
      amplification of Sat_129

<400> SEQUENCE: 7
```
tcacatgttc gggacttaag gtat                                          24

<210> SEQ ID NO 8
<211> LENGTH: 21
<212> TYPE: DNA
<213> ORGANISM: Artificial
<220> FEATURE:
<223> OTHER INFORMATION: synthetic oligonucleotide primer for
     amplification of Satt155

<400> SEQUENCE: 8
agatccaaca cctggcctaa t                                             21

<210> SEQ ID NO 9
<211> LENGTH: 21
<212> TYPE: DNA
<213> ORGANISM: Artificial
<220> FEATURE:
<223> OTHER INFORMATION: synthetic oligonucleotide primer for
     amplification of Satt155

<400> SEQUENCE: 9
gctgcacaat tcattccatt t                                             21

<210> SEQ ID NO 10
<211> LENGTH: 24
<212> TYPE: DNA
<213> ORGANISM: Artificial
<220> FEATURE:
<223> OTHER INFORMATION: synthetic oligonucleotide primer for
     amplification of Satt231

<400> SEQUENCE: 10
gcgtgtgcaa aatgttcatc atct                                          24

<210> SEQ ID NO 11
<211> LENGTH: 24
<212> TYPE: DNA
<213> ORGANISM: Artificial
<220> FEATURE:
<223> OTHER INFORMATION: synthetic oligonucleotide primer for
     amplification of Satt231

<400> SEQUENCE: 11
ggcacgaatc aacatcaaaa cttc                                          24

<210> SEQ ID NO 12
<211> LENGTH: 20
<212> TYPE: DNA
<213> ORGANISM: Artificial
<220> FEATURE:
<223> OTHER INFORMATION: synthetic oligonucleotide primer for
     amplification of P1047

<400> SEQUENCE: 12
tcgcttttaa tgacctcgac                                               20

<210> SEQ ID NO 13
<211> LENGTH: 21
<212> TYPE: DNA
<213> ORGANISM: Artificial
<220> FEATURE:
<223> OTHER INFORMATION: synthetic oligonucleotide primer for
     amplification of P1047

<400> SEQUENCE: 13
cggaggattt gtcatagatt c                                             21

```
<210> SEQ ID NO 14
<211> LENGTH: 24
<212> TYPE: DNA
<213> ORGANISM: Artificial
<220> FEATURE:
<223> OTHER INFORMATION: synthetic oligonucleotide primer for
      amplification of Satt311

<400> SEQUENCE: 14
gggggaacca caaaaatctt aatc                                          24

<210> SEQ ID NO 15
<211> LENGTH: 24
<212> TYPE: DNA
<213> ORGANISM: Artificial
<220> FEATURE:
<223> OTHER INFORMATION: synthetic oligonucleotide primer for
      amplification of Satt311

<400> SEQUENCE: 15
gttgaagctc aggctgtgat gaat                                          24

<210> SEQ ID NO 16
<211> LENGTH: 24
<212> TYPE: DNA
<213> ORGANISM: Artificial
<220> FEATURE:
<223> OTHER INFORMATION: synthetic oligonucleotide primer for
      amplification of Satt329

<400> SEQUENCE: 16
gcgggacgca aaattggatt tagt                                          24

<210> SEQ ID NO 17
<211> LENGTH: 24
<212> TYPE: DNA
<213> ORGANISM: Artificial
<220> FEATURE:
<223> OTHER INFORMATION: synthetic oligonucleotide primer for
      amplification of Satt329

<400> SEQUENCE: 17
gcgccgaata aaacgtgaga actg                                          24

<210> SEQ ID NO 18
<211> LENGTH: 19
<212> TYPE: DNA
<213> ORGANISM: Artificial
<220> FEATURE:
<223> OTHER INFORMATION: synthetic oligonucleotide primer for
      amplification of PHP10118C

<400> SEQUENCE: 18
gactgcgtac caattcaca                                                19

<210> SEQ ID NO 19
<211> LENGTH: 19
<212> TYPE: DNA
<213> ORGANISM: Artificial
<220> FEATURE:
<223> OTHER INFORMATION: synthetic oligonucleotide primer for
      amplification of PHP10118C

<400> SEQUENCE: 19
gatgagtcct gagtaacac                                                19
```

-continued

```
<210> SEQ ID NO 20
<211> LENGTH: 27
<212> TYPE: DNA
<213> ORGANISM: Artificial
<220> FEATURE:
<223> OTHER INFORMATION: synthetic oligonucleotide primer for
      amplification of Satt523

<400> SEQUENCE: 20
gcgatttctt ccttgaagaa ttttctg                                         27

<210> SEQ ID NO 21
<211> LENGTH: 27
<212> TYPE: DNA
<213> ORGANISM: Artificial
<220> FEATURE:
<223> OTHER INFORMATION: synthetic oligonucleotide primer for
      amplification of Satt523

<400> SEQUENCE: 21 gcgcttttc ggctgttatt tttaact                                          27

<210> SEQ ID NO 22
<211> LENGTH: 21
<212> TYPE: DNA
<213> ORGANISM: Artificial
<220> FEATURE:
<223> OTHER INFORMATION: synthetic oligonucleotide primer for
      amplification of Satt556

<400> SEQUENCE: 22
gcgataaaac ccgataaata a                                               21

<210> SEQ ID NO 23
<211> LENGTH: 21
<212> TYPE: DNA
<213> ORGANISM: Artificial
<220> FEATURE:
<223> OTHER INFORMATION: synthetic oligonucleotide primer for
      amplification of Satt556

<400> SEQUENCE: 23
gcgttgtgca ccttgttttc t                                               21

<210> SEQ ID NO 24
<211> LENGTH: 280
<212> TYPE: DNA
<213> ORGANISM: Glycine max

<400> SEQUENCE: 24
ttaacatcgt atatatggat tgcttatgtg caatggcaga tccaacacct ggcctaattg     60
gggaatttat ttttaaaaaa tattattatt attattatta ttattattat tattattatt   120
attattatta ttattattaa aacaaaaatt aaaattaacc acagtgagct aaaaatggaa   180
tgaattgtgc agcaaaataa attataaaat tacttaatga aatgaaaaaa agtaaaactt   240
aagaaaaaaa aaagctagtg ataaaaaatt aggagttgtg                         280

<210> SEQ ID NO 25
<211> LENGTH: 576
<212> TYPE: DNA
<213> ORGANISM: Glycine max
<220> FEATURE:
<221> NAME/KEY: misc_feature
<222> LOCATION: (117)..(117)
<223> OTHER INFORMATION: unknown (a,c,g or t)
<220> FEATURE:
<221> NAME/KEY: misc_feature
```

```
<222> LOCATION: (488)..(488)
<223> OTHER INFORMATION: unknown (a,c,g or t)

<400> SEQUENCE: 25
tttagcgtgg aattaagttt aaacttaggt taaaagagaa taacttaaat taatattctc      60
aaatttagat attaaaaata taatttcttt aaatttggat taaagaaaat ttgtggntct     120
tagttatttg atagtttgac cttatttcag tacaagtcgg gtgaataata ataataataa     180
taataataat aataataata ataataataa taataataat aataataata ataataatag     240
aaccaacctt tttcttttgc caagaaaaat aataccttaa gtcccgaaca tgtgaagata     300
actcacaatt cttacrcggt ttctaactga tacctcctcc acccgacgat attgctagaa     360
acgagaattt ataaacttat gaaaatttta tcattaaatt aataatatc actctttaaa      420 attaaatttt gtatcaaaca attgacatat ctcatttgat tttcagatca ttatgctaag     480
cgcttcanca aataaattat ccagattgaa agagcaggcc gaggaatacg cagctctgat     540
catggaagag ttagaccctg aaagacttcg ctacat                                576

<210> SEQ ID NO 26
<211> LENGTH: 983
<212> TYPE: DNA
<213> ORGANISM: Glycine max
<220> FEATURE:
<221> NAME/KEY: misc_feature
<222> LOCATION: (16)..(16)
<223> OTHER INFORMATION: unknown (a,c,g or t)
<220> FEATURE:
<221> NAME/KEY: misc_feature
<222> LOCATION: (385)..(385)
<223> OTHER INFORMATION: unknown (a,c,g or t)
<220> FEATURE:
<221> NAME/KEY: misc_feature
<222> LOCATION: (389)..(389)
<223> OTHER INFORMATION: unknown (a,c,g or t)
<220> FEATURE:
<221> NAME/KEY: misc_feature
<222> LOCATION: (394)..(394)
<223> OTHER INFORMATION: unknown (a,c,g or t)
<220> FEATURE:
<221> NAME/KEY: misc_feature
<222> LOCATION: (401)..(401)
<223> OTHER INFORMATION: unknown (a,c,g or t)
<220> FEATURE:
<221> NAME/KEY: misc_feature
<222> LOCATION: (407)..(407)
<223> OTHER INFORMATION: unknown (a,c,g or t)
<220> FEATURE:
<221> NAME/KEY: misc_feature
<222> LOCATION: (409)..(409)
<223> OTHER INFORMATION: unknown (a,c,g or t)
<220> FEATURE:
<221> NAME/KEY: misc_feature
<222> LOCATION: (424)..(424)
<223> OTHER INFORMATION: unknown (a,c,g or t)
<220> FEATURE:
<221> NAME/KEY: misc_feature
<222> LOCATION: (431)..(431)
<223> OTHER INFORMATION: unknown (a,c,g or t)

<400> SEQUENCE: 26
ccgtgttatg tcgtcnttgg gtcaaattgg gtgccatgat tatgaccaat agcttggctt      60
tcattcagag tgccttgact gagcattatc agtagcatgc cttctaccat taagtcactc     120
gaaccagttg caagtagttg gtctctacaa cgaaaaatga agaaccatga acgacgaaaa     180
atgaagaaaa atagaaccac taagaacgaa aaatggaacc aacaacaaca cttacagccc     240
agtttcgaaa tcctttaaat agagaaaata atatcactat tataatttag gaatgttcat     300
ggttatcaat tactcacgaa cttgaatgga cgcaaaattg gatttagtat ttttttgcatt    360
```

```
gaatcaaatc ttatctaatt ctttncaanc catngatttt ngggtgnant cacatatttt      420
tatntgtcta natattatta ttattattat tattattatt attattatta ttattattat      480
tattattatt attattatta ttaaattttt taaatatcaa ttactattac tatcataact      540
tagtaaaagt gacattatct tcttttttt ttcagttctc acgttttatt cggttacttt       600
tacgaagatt aggattttaa ctgccatttg attttaaaaa tatctctttt aattttaat      660 taatttattt caaactattt tagatttagt taaagtttta tttgtattac tcatttaact      720
attagagaac attagaattt tcaaaatgct ctaatagttt tagtttttta aggctccgtg      780
agtgtggtga ttaaatttat ttattatatt tcaattttta aatcatgttt aatataattt      840
catttagttt caaatataag caacaaaatc ccttactttt gggtctcaaa tataaataaa      900
ttttaattac ttatgtctta tttaatgaaa ctctctcaaa aatatcattt tttaatgagg      960
tcaaagactt ttttatgttt gat                                              983

<210> SEQ ID NO 27
<211> LENGTH: 293
<212> TYPE: DNA
<213> ORGANISM: Glycine max

<400> SEQUENCE: 27
tcccattgct tcgggccaca agtctacgac tataataatt cgccaaacag agtgtaccca       60
atatttttca aaagcaaaca acacagaaga atcaccacac ataacaagca atcataaccc      120
agatacagac aataaaaccc gataaataag atttcatgaa taataataat aataataata      180
ataataataa taataataat actcaaagac caaaatttca ttttcgaaac atgatatagg      240
cttcagagat gaacgaacat aaaatacata agaaaacaag gtgcacaatt agg             293

<210> SEQ ID NO 28
<211> LENGTH: 455
<212> TYPE: DNA
<213> ORGANISM: Glycine max
<220> FEATURE:
<221> NAME/KEY: misc_feature
<222> LOCATION: (11)..(11)
<223> OTHER INFORMATION: unknown (a,c,g or t)
<220> FEATURE:
<221> NAME/KEY: misc_feature
<222> LOCATION: (96)..(96)
<223> OTHER INFORMATION: unknown (a,c,g or t)
<220> FEATURE:
<221> NAME/KEY: misc_feature
<222> LOCATION: (180)..(182)
<223> OTHER INFORMATION: unknown (a,c,g or t)
<220> FEATURE:
<221> NAME/KEY: misc_feature
<222> LOCATION: (195)..(195)
<223> OTHER INFORMATION: unknown (a,c,g or t)
<220> FEATURE:
<221> NAME/KEY: misc_feature
<222> LOCATION: (202)..(202)
<223> OTHER INFORMATION: unknown (a,c,g or t)
<220> FEATURE:
<221> NAME/KEY: misc_feature
<222> LOCATION: (216)..(217)
<223> OTHER INFORMATION: unknown (a,c,g or t)
<220> FEATURE:
<221> NAME/KEY: misc_feature
<222> LOCATION: (232)..(233)
<223> OTHER INFORMATION: unknown (a,c,g or t)
<220> FEATURE:
<221> NAME/KEY: misc_feature
<222> LOCATION: (238)..(238)
<223> OTHER INFORMATION: unknown (a,c,g or t)
<220> FEATURE:
<221> NAME/KEY: misc_feature
```

```
<222> LOCATION: (247)..(247)
<223> OTHER INFORMATION: unknown (a,c,g or t)
<220> FEATURE:
<221> NAME/KEY: misc_feature
<222> LOCATION: (250)..(250)
<223> OTHER INFORMATION: unknown (a,c,g or t)
<220> FEATURE:
<221> NAME/KEY: misc_feature
<222> LOCATION: (254)..(254)
<223> OTHER INFORMATION: unknown (a,c,g or t)
<220> FEATURE:
<221> NAME/KEY: misc_feature
<222> LOCATION: (259)..(259)
<223> OTHER INFORMATION: unknown (a,c,g or t)
<220> FEATURE:
<221> NAME/KEY: misc_feature
<222> LOCATION: (261)..(261)
<223> OTHER INFORMATION: unknown (a,c,g or t)
<220> FEATURE:
<221> NAME/KEY: misc_feature
<222> LOCATION: (264)..(264)
<223> OTHER INFORMATION: unknown (a,c,g or t)
<220> FEATURE:
<221> NAME/KEY: misc_feature
<222> LOCATION: (281)..(281)
<223> OTHER INFORMATION: unknown (a,c,g or t)
<220> FEATURE:
<221> NAME/KEY: misc_feature
<222> LOCATION: (287)..(287)
<223> OTHER INFORMATION: unknown (a,c,g or t)
<220> FEATURE:
<221> NAME/KEY: misc_feature
<222> LOCATION: (299)..(299)
<223> OTHER INFORMATION: unknown (a,c,g or t)
<220> FEATURE:
<221> NAME/KEY: misc_feature
<222> LOCATION: (307)..(307)
<223> OTHER INFORMATION: unknown (a,c,g or t)
<220> FEATURE:
<221> NAME/KEY: misc_feature
<222> LOCATION: (309)..(309)
<223> OTHER INFORMATION: unknown (a,c,g or t)
<220> FEATURE:
<221> NAME/KEY: misc_feature
<222> LOCATION: (315)..(315)
<223> OTHER INFORMATION: unknown (a,c,g or t)
<220> FEATURE:
<221> NAME/KEY: misc_feature
<222> LOCATION: (320)..(321)
<223> OTHER INFORMATION: unknown (a,c,g or t)
<220> FEATURE:
<221> NAME/KEY: misc_feature
<222> LOCATION: (334)..(334)
<223> OTHER INFORMATION: unknown (a,c,g or t)
<220> FEATURE:
<221> NAME/KEY: misc_feature
<222> LOCATION: (338)..(338)
<223> OTHER INFORMATION: unknown (a,c,g or t)
<220> FEATURE:
<221> NAME/KEY: misc_feature
<222> LOCATION: (340)..(340)
<223> OTHER INFORMATION: unknown (a,c,g or t)
<220> FEATURE:
<221> NAME/KEY: misc_feature
<222> LOCATION: (343)..(343)
<223> OTHER INFORMATION: unknown (a,c,g or t)
<220> FEATURE:
<221> NAME/KEY: misc_feature
<222> LOCATION: (362)..(362)
<223> OTHER INFORMATION: unknown (a,c,g or t)
<220> FEATURE:
<221> NAME/KEY: misc_feature
<222> LOCATION: (372)..(372)
<223> OTHER INFORMATION: unknown (a,c,g or t)
<220> FEATURE:
<221> NAME/KEY: misc_feature
<222> LOCATION: (378)..(378)
<223> OTHER INFORMATION: unknown (a,c,g or t)
<220> FEATURE:
<221> NAME/KEY: misc_feature
```

```
<222> LOCATION: (383)..(383)
<223> OTHER INFORMATION: unknown (a,c,g or t)
<220> FEATURE:
<221> NAME/KEY: misc_feature
<222> LOCATION: (389)..(389)
<223> OTHER INFORMATION: unknown (a,c,g or t)
<220> FEATURE:
<221> NAME/KEY: misc_feature
<222> LOCATION: (391)..(391)
<223> OTHER INFORMATION: unknown (a,c,g or t)
<220> FEATURE:
<221> NAME/KEY: misc_feature
<222> LOCATION: (397)..(397)
<223> OTHER INFORMATION: unknown (a,c,g or t)
<220> FEATURE:
<221> NAME/KEY: misc_feature
<222> LOCATION: (401)..(401)
<223> OTHER INFORMATION: unknown (a,c,g or t)
<220> FEATURE:
<221> NAME/KEY: misc_feature
<222> LOCATION: (403)..(403)
<223> OTHER INFORMATION: unknown (a,c,g or t)
<220> FEATURE:
<221> NAME/KEY: misc_feature
<222> LOCATION: (406)..(406)
<223> OTHER INFORMATION: unknown (a,c,g or t)
<220> FEATURE:
<221> NAME/KEY: misc_feature
<222> LOCATION: (410)..(411)
<223> OTHER INFORMATION: unknown (a,c,g or t)
<220> FEATURE:
<221> NAME/KEY: misc_feature
<222> LOCATION: (415)..(415)
<223> OTHER INFORMATION: unknown (a,c,g or t)
<220> FEATURE:
<221> NAME/KEY: misc_feature
<222> LOCATION: (424)..(424)
<223> OTHER INFORMATION: unknown (a,c,g or t)
<220> FEATURE:
<221> NAME/KEY: misc_feature
<222> LOCATION: (429)..(429)
<223> OTHER INFORMATION: unknown (a,c,g or t)
<220> FEATURE:
<221> NAME/KEY: misc_feature
<222> LOCATION: (434)..(434)
<223> OTHER INFORMATION: unknown (a,c,g or t)
<220> FEATURE:
<221> NAME/KEY: misc_feature
<222> LOCATION: (438)..(438)
<223> OTHER INFORMATION: unknown (a,c,g or t)
<220> FEATURE:
<221> NAME/KEY: misc_feature
<222> LOCATION: (449)..(449)
<223> OTHER INFORMATION: unknown (a,c,g or t)
<220> FEATURE:
<221> NAME/KEY: misc_feature
<222> LOCATION: (443)..(443)
<223> OTHER INFORMATION: unknown (a,c,g or t)
<220> FEATURE:
<221> NAME/KEY: misc_feature
<222> LOCATION: (455)..(455)
<223> OTHER INFORMATION: unknown (a,c,g or t)
<220> FEATURE:
<221> NAME/KEY: misc_feature
<222> LOCATION: (381)..(381)
<223> OTHER INFORMATION: unknown (a,c,g or t)
<220> FEATURE:
<221> NAME/KEY: misc_feature
<222> LOCATION: (330)..(331)
<223> OTHER INFORMATION: unknown (a,c,g or t)

<400> SEQUENCE: 28
aaaattataa ntataataat gaaaatgatt aacaatgttt atgataatta tacatattat      60
attttttact gcataggtat tattattatt attatnatta ttattattat tattattatt     120
attattatta ttattattaa actaattgtt attaactgat gcaagtaata aaaaaactan     180
nnatcagcga tgaanatgaa antgctaaaa atattnnata cacaactgtg annaggtnag     240
```

```
atgtaantgn ggcnccctna ntgngctcaa tgtgtaattg nggtctncta ttccaagana    300
gagacangng gtccntctan ntcagaaaan ncanaatngn ggncctccat atttataaaa    360
angtgtaacc cngcgggnca ncntcaccnc natctangcc ncntcncttn nattnctcac    420
atantaacna accnaccnct ccncgctgnt acttn                              455
```

<210> SEQ ID NO 29
<211> LENGTH: 693
<212> TYPE: DNA
<213> ORGANISM: Glycine max

<400> SEQUENCE: 29

```
acaaagaatt cattttcctc cattacttgg tctattttca tcttcaattc agtgttttc     60 acttctaaca tgacattctt ctttgttata tcatcctgct aatcaaagaa gctaatttta   120
tatgtaatga attaatgtgg agtagaaaag ataaagatca ataatctatg acaagaccga   180
aaagattgag gtaaaataaa atctcacatg ataaaagctc aacttagggg gaaccacaaa   240
aatcttaatc aaacaaacca caaaagatg aaacaaaata gtaatagtaa tataatataa    300
caatgccaca tatatattat actaataaac aataataata ataataataa taataataat   360
aataataata tatgtagtag tgaattcatc acagcctgag cttcaactta caactactgc   420
tagaaattct aatatcatta ctagcaccaa gattatccac ctcaagccta cacctaaccc   480
tgaacttgac tttgaagagc ttcagcttac caagcttaac tctcacaggc taattcacct   540
taagattgag aggaacattg ttggtctgtt gcaactactc ctgaattcta ttgaccaaac   600
cacttgcatc atgtgcttga ccagttagag gcaaatcaag cactgttgtg ttcctatgac   660
cctggtagaa ctttggcaag gacccttcac aca                                693
```

<210> SEQ ID NO 30
<211> LENGTH: 374
<212> TYPE: DNA
<213> ORGANISM: Glycine max

<400> SEQUENCE: 30

```
ggatccattc cactttttgt acaatatttt atgcattaaa tacttagaat tatatacata    60
ataacagtat attatatata tatatatata tatatatata tatatatata tatatatata   120
tatatatata tatatata tattgacaga cctatatgcg ttagaggtgg ataaatgtat     180
ctctttattt taataaaatt acatatattt atcttaaaat tatataattt ataccactaa   240
tggatgtttg aacttgttat tgttagaaca aatctctttt aacctgtgat attacaaact   300
acaaagaaac acgggttatt aataaaatgc gaaaattaca gatcaaaaca tacctccagc   360
cattgctatg aaga                                                     374
```

<210> SEQ ID NO 31
<211> LENGTH: 529
<212> TYPE: DNA
<213> ORGANISM: Glycine max
<220> FEATURE:
<221> NAME/KEY: misc_feature
<222> LOCATION: (471)..(472)
<223> OTHER INFORMATION: unknown (a,c,g or t)
<220> FEATURE:
<221> NAME/KEY: misc_feature
<222> LOCATION: (483)..(483)
<223> OTHER INFORMATION: unknown (a,c,g or t)
<220> FEATURE:
<221> NAME/KEY: misc_feature
<222> LOCATION: (528)..(528)
<223> OTHER INFORMATION: unknown (a,c,g or t)

```
<400> SEQUENCE: 31
ttattgtttt ttatactgtt atatgtgcaa aatgttcatc atcttttct gatccctaat      60 ttctgcttgt gaaactggct gattattttt tattagaaat tagaaataaa tgcactttaa    120
taataataat aataataata ataataataa taataataat aataataata ataataataa    180
taataataat aataataata ataataataa taatagtaat ctgtgatggg aacagaagga    240
agttttgatg ttgattcgtg gccttttttt tcttttcatt ttttgtctaa tttttaaatg    300
agttactttt gcatgttttt tcttctccgc taattttggt gtggtagatt cctgatgtct    360
gttagagatt ttttgggga ataagaataa tatttatctg ttttcctctc ctgttgttta    420
attttcctat gctttttat gactaggttg taacttttat ttatttatta nnttgacaag     480
gtntcaactt tattctgttt gatttgaatc cgattctgga tttttatnc               529

<210> SEQ ID NO 32
<211> LENGTH: 591
<212> TYPE: DNA
<213> ORGANISM: Glycine max
<220> FEATURE:
<221> NAME/KEY: misc_feature
<222> LOCATION: (162)..(162)
<223> OTHER INFORMATION: unknown (a,c,g or t)
<220> FEATURE:
<221> NAME/KEY: misc_feature
<222> LOCATION: (193)..(193)
<223> OTHER INFORMATION: unknown (a,c,g or t)

<400> SEQUENCE: 32
gaactctggt ccatcccttc gtccaccaaa tattcaaatg ttcctttta gggttatctt      60 tttccttcca ccattttaa catctctttc tcctttgcat tattattatt attattatta    120
ttattattat tattattatt attattatta acctataccct anaacaatcc tctattttaa    180
ttaaataatc ccncttagta ttcatgtctc tctctctata ggaaacttta cactcgtatg    240
attactatct tgtacggaat cgacgggtag tcgacacttg ttaactgact atcactttac    300
acatattatt attgtgaaca attatcaact cggtcactat catcttttat aagacaaaag    360
accatgtaag aataggaaag tcatatttg tttacaatat acaccttaga caaatatcta    420
tatcctttat acaaacaagg ctctaacaca tgcagaaagt accaaaatgc cctaacttt    480 ctgaggtgtc gtcgtctggg ggattttgtt cctgcccaaa atggttcgtg tgggttttta    540
gaatttctta tggaattggg atacgtggta cgcgtacacg cgttttggtg g             591

<210> SEQ ID NO 33
<211> LENGTH: 732
<212> TYPE: DNA
<213> ORGANISM: Glycine max

<400> SEQUENCE: 33
gggtcaacaa aagttgatca tgaaattgtg gagctcattt cggccaagaa aattaatcaa      60
ctccagttaa acttgtgttt atcctataaa ttgtaaaatt attgcttatc atgcttattg    120
aaaaaattac atgattatct caatgtactg tacatttta ttgtaaattt ttttatgtta    180
tattatatag tgcacgtttt tgatatagct aatttcttcc ttgaagaatt ttctgctgta    240
aatttaattg ataaaataat agaaagactt ttttaaagaa atttaataat aataataata    300
ataataataa taataataat aataataagt tctattattt gcgaataaag ttaaaaataa    360
cagccgaaaa agttcaacaa atttacaact tttgcatgtg aaagctacaa cttcaatttt    420
tcttttatgt aagtcactaa acttacatat atttaacaaa ttttgcaaat atatcttgca    480
```

```
taagtaaatt ataaaataaa tttggtttac atgtgtttat tagaataaaa atttaaaatt      540
aatataatta aattatattt ttatataaag aatggatcaa aattaaattt atatttttat      600
aagtagagtg cttttattta aatatacata ctttgtcaga atgtatatgg ctacacttcg      660
taaacagaca aactagcaca cggtcacata tttttcaatt caaaattgtg acgatgaaga      720
ataaagtatc aa                                                         732
```